(12) United States Patent
Nicacio et al.

(10) Patent No.: US 12,239,842 B2
(45) Date of Patent: Mar. 4, 2025

(54) METHOD AND APPARATUS FOR INHIBITING THE GROWTH OF PROLIFERATING CELLS OR VIRUSES

(71) Applicant: ALTERNATING CURRENT TREATMENT THERAPY MEDICAL INC., Lakeside, MT (US)

(72) Inventors: Rodolfo Nicacio, Richland, WA (US); Michael Colton, Richland, WA (US); Solomon Berecha Erpasa, Bellevue, WA (US)

(73) Assignee: ACTT Medical Inc., Kennewick, WA (US)

( * ) Notice: Subject to any disclaimer, the term of this patent is extended or adjusted under 35 U.S.C. 154(b) by 1041 days.

(21) Appl. No.: 17/158,755

(22) Filed: Jan. 26, 2021

(65) Prior Publication Data

US 2021/0228895 A1    Jul. 29, 2021

Related U.S. Application Data

(60) Provisional application No. 63/045,830, filed on Jun. 29, 2020, provisional application No. 62/987,344, (Continued)

(51) Int. Cl.
*A61N 1/00* (2006.01)
*A61N 1/04* (2006.01)
(Continued)

(52) U.S. Cl.
CPC ............. *A61N 1/40* (2013.01); *A61N 1/0456* (2013.01); *A61N 1/36002* (2017.08);
(Continued)

(58) Field of Classification Search
CPC .... A61N 1/40; A61N 1/0456; A61N 1/36002; A61N 1/3601; A61N 1/0476;
(Continued)

(56) References Cited

U.S. PATENT DOCUMENTS

| 5,928,940 A | 7/1999 | Sampath et al. |
| 2004/0193003 A1 | 9/2004 | Mechlenburg et al. |

(Continued)

FOREIGN PATENT DOCUMENTS

EP    0 894 473 A2    2/1999

*Primary Examiner* — Scott M. Getzow
(74) *Attorney, Agent, or Firm* — BOOTH UDALL FULLER, PLC

(57) ABSTRACT

The present invention provides a method of inhibiting the growth of proliferating cells or viruses in living tissue, the method comprising: applying mid-level frequency AC current electromagnetic signals to the living tissue with a transducer comprising a magnetically conductive material passing through a conduction ring energized by an electrical signal to create the mid-level frequency AC current electromagnetic signals within the living tissue; wherein the mid-level frequency AC current electromagnetic signals have a frequency in the range of about 50 kHz to about 300 kHz and are produced with an AC voltage generator; and circulating fluid in the living tissue provide a secondary coil for the transmission of the mid-level frequency AC current electromagnetic signals.

12 Claims, 31 Drawing Sheets

Related U.S. Application Data filed on Mar. 9, 2020, provisional application No. 62/966,513, filed on Jan. 27, 2020.

(51) Int. Cl.

| | |
|---|---|
| *A61N 1/36* | (2006.01) |
| *A61N 1/40* | (2006.01) |
| *A61N 2/02* | (2006.01) |
| *H02J 50/10* | (2016.01) |
| *H01F 1/34* | (2006.01) |
| *H01F 27/28* | (2006.01) |
| *H01F 38/14* | (2006.01) |

(52) U.S. Cl.
CPC ............ *A61N 1/3601* (2013.01); *A61N 2/02* (2013.01); *H02J 50/10* (2016.02); *H01F 1/34* (2013.01); *H01F 27/2823* (2013.01); *H01F 38/14* (2013.01)

(58) Field of Classification Search
CPC ....... A61N 1/36014; A61N 2/02; H02J 50/10; H01F 1/34; H01F 27/2823; H01F 38/14
See application file for complete search history.

(56) References Cited

U.S. PATENT DOCUMENTS

| | | | |
|---|---|---|---|
| 2009/0027050 A1 | 1/2009 | Garwood et al. | |
| 2011/0077451 A1 | 3/2011 | Marchitto et al. | |
| 2011/0137229 A1* | 6/2011 | Palti .................... | A61N 1/0428 604/20 |
| 2012/0016174 A1* | 1/2012 | De Taboada ............ | A61N 5/04 607/3 |
| 2012/0267986 A1 | 10/2012 | Galluzzo et al. | |
| 2019/0001151 A1* | 1/2019 | Abdolahad ............... | A61N 5/10 |
| 2019/0117969 A1* | 4/2019 | Schmidt ............... | A61N 1/0424 |
| 2019/0126041 A1* | 5/2019 | Kerselaers ......... | A61N 1/36003 |
| 2019/0255344 A1* | 8/2019 | Carter ................ | A61N 1/0484 |
| 2020/0230408 A1* | 7/2020 | Errico ............... | A61N 1/36014 |

* cited by examiner

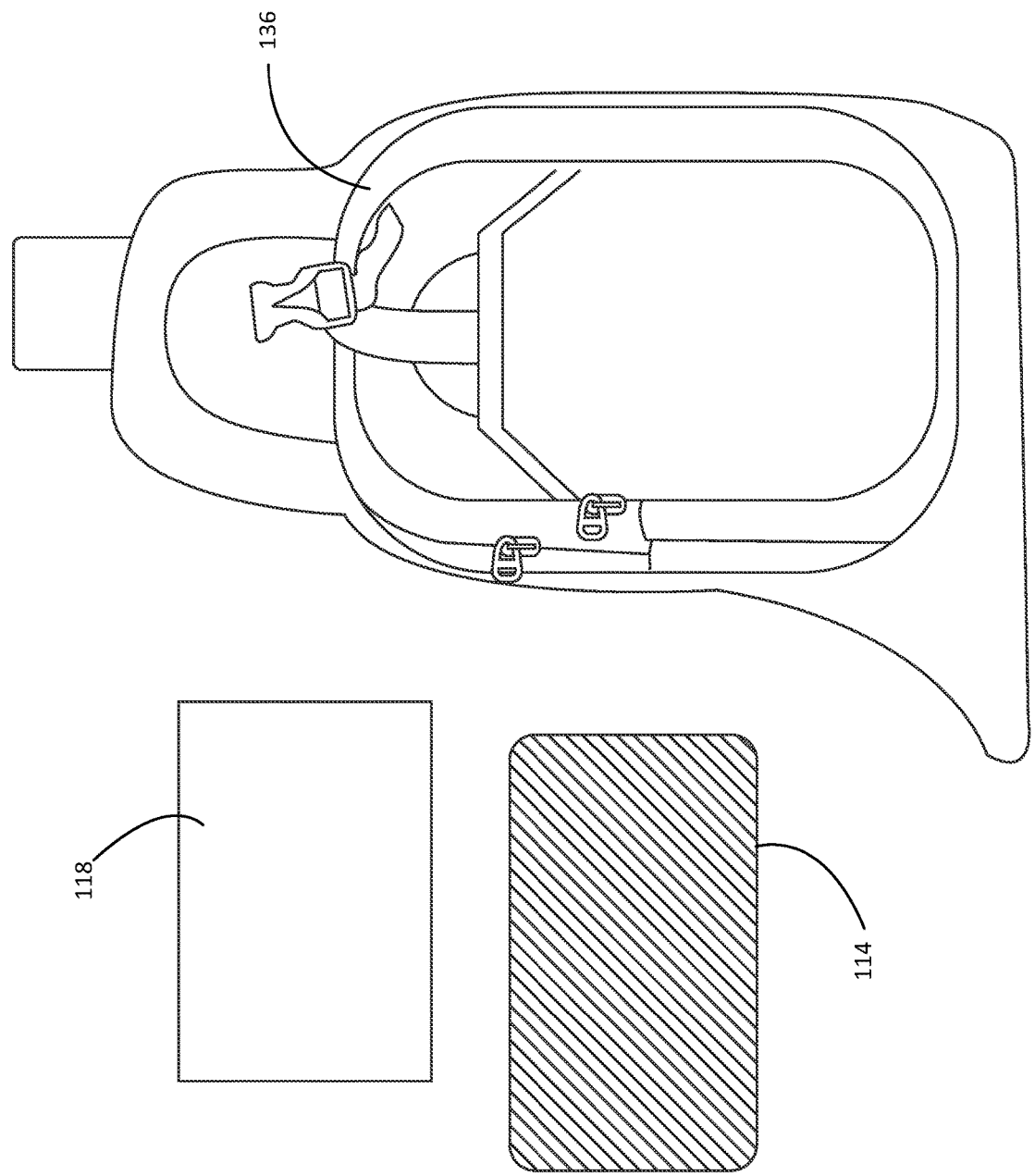

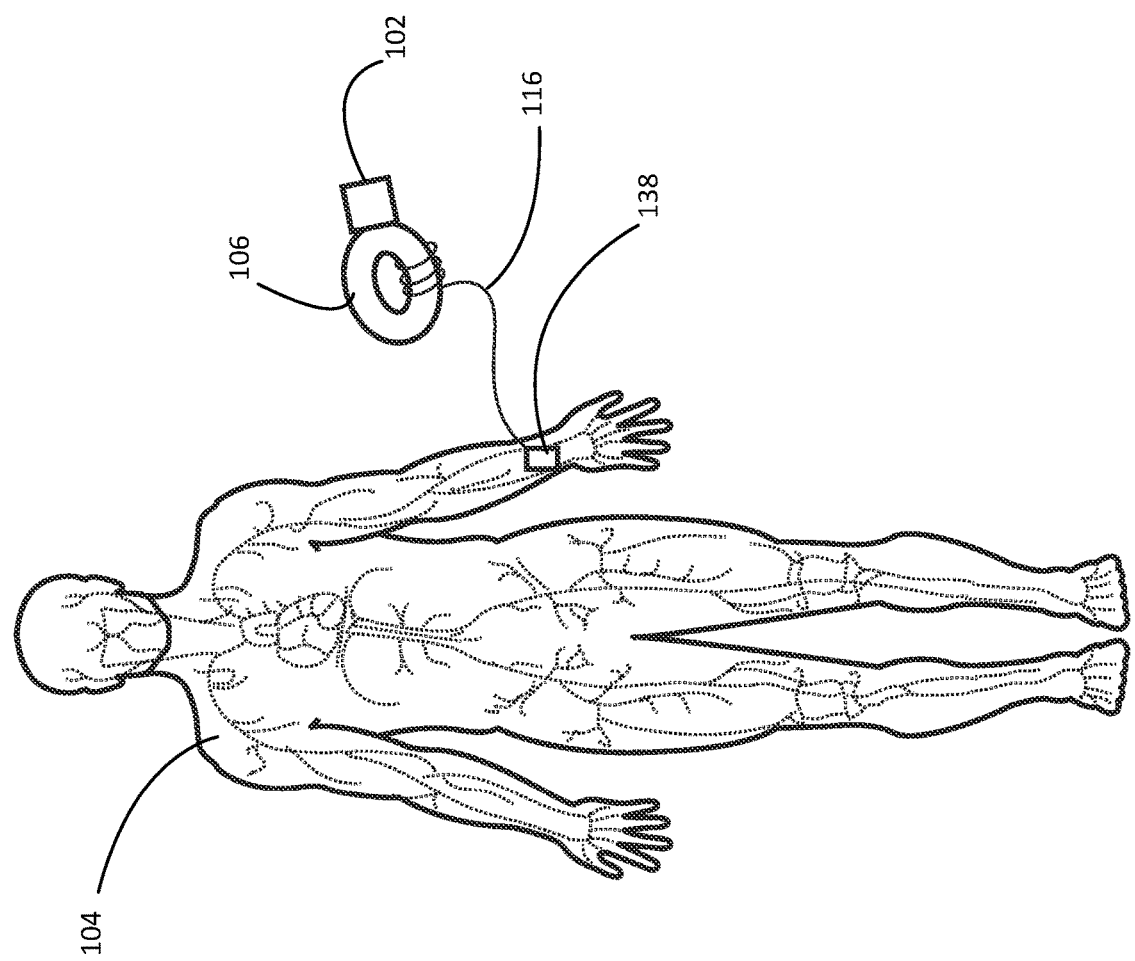

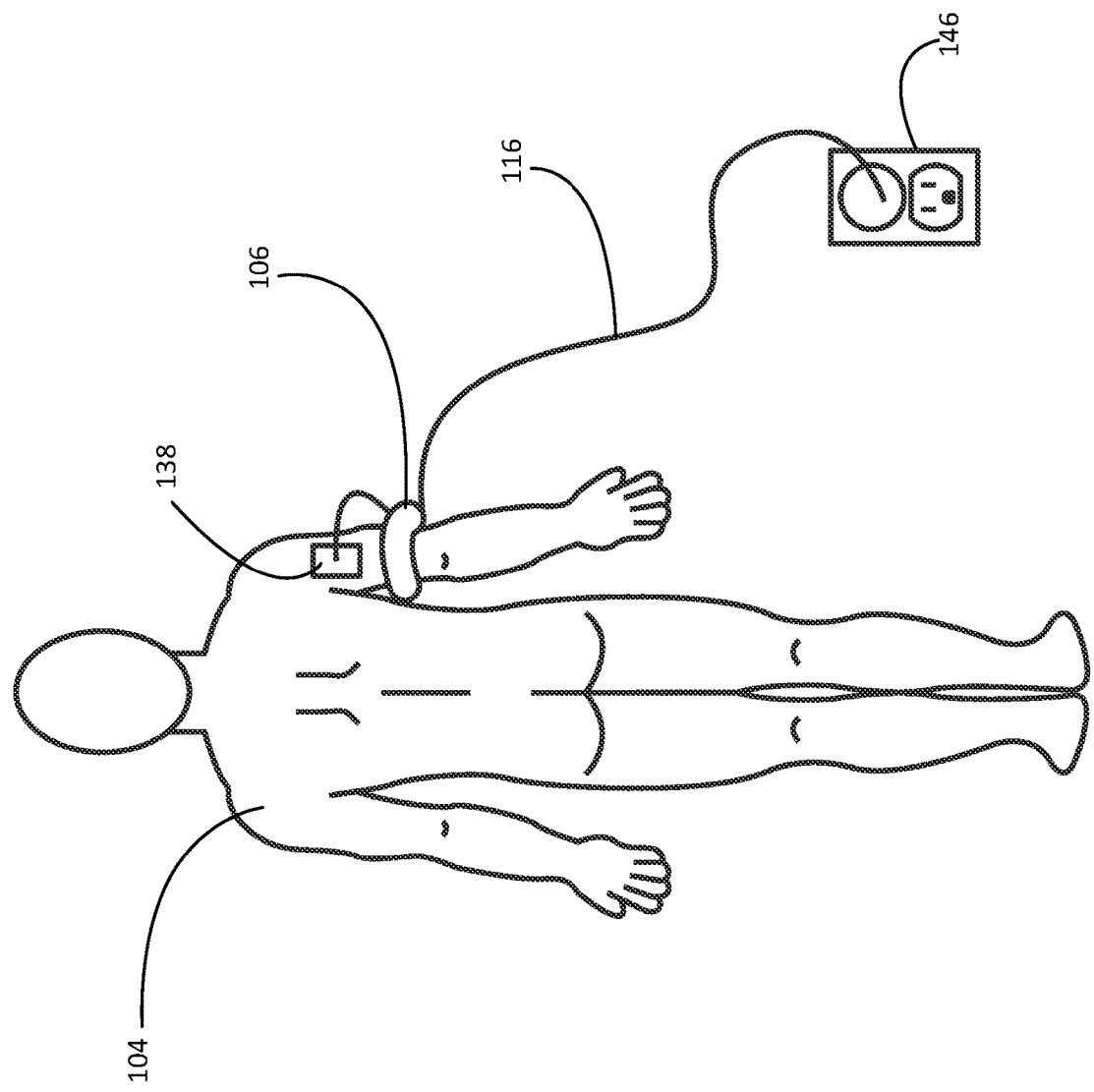

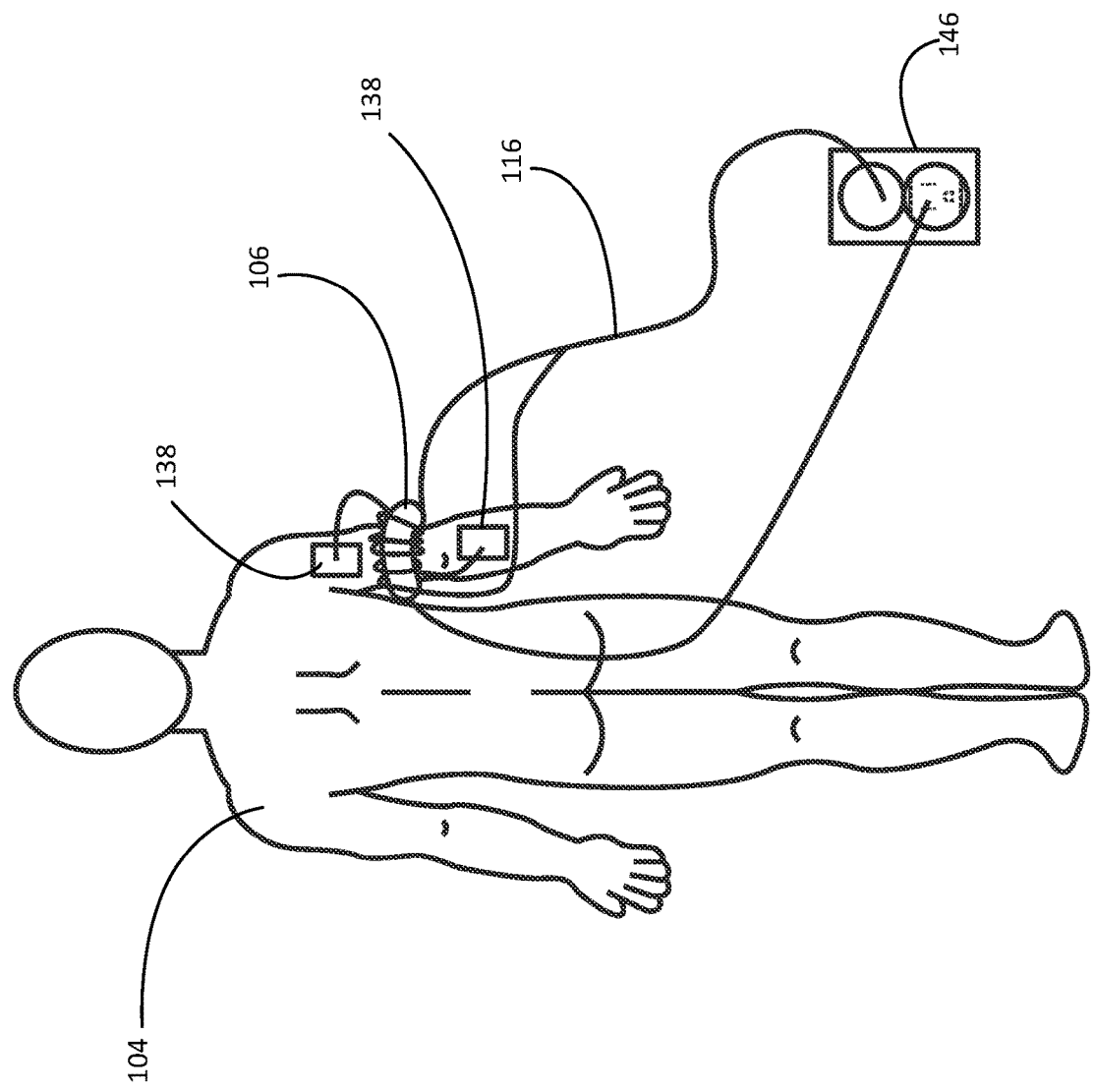

METHOD AND APPARATUS FOR INHIBITING THE GROWTH OF PROLIFERATING CELLS OR VIRUSES

CROSS-REFERENCE TO RELATED APPLICATIONS

This application claims priority to U.S. Provisional Patent Application No. 62/966,513, filed Jan. 27, 2020, U.S. Provisional Patent Application No. 62/987,344, filed Mar. 9, 2020, and U.S. Provisional Patent Application No. 63/045,830, filed Jun. 29, 2020, the contents of which are incorporated herein by reference in their entireties.

TECHNICAL FIELD

This application relates to methods and apparatuses for inhibiting the growth of proliferating cells such as cancer cells or infectious pathogens, including viruses, by applying mid-level frequency AC current electromagnetic signals to living tissue.

BACKGROUND

Cancer is a group of diseases involving abnormal cell growth with the potential to invade or spread to other parts of the body. In 2014, there were an estimated 1,665,540 new cancer cases diagnosed and 585,720 cancer deaths in the US. $6 billion of tax-payer funds are cycled through various federal agencies for cancer research including the National Cancer Institute (NCI). The NCI states that the medical costs of cancer care are $125 billion with a projected 39 percent increase to $173 billion by 2020.

Because cancer is a class of diseases, it is unlikely that there will be a single "cure for cancer" any more than there will be a single treatment for all infectious diseases. One method for treating cancer is with Tumor-Treating Therapy, also known as TTF or TTFields.

As with many cancer treatments, TTF target rapidly dividing tumor cells. During mitosis, cells that are exposed to TTF exhibit uncontrolled membrane blebbing at the onset of anaphase, resulting in aberrant mitotic exit. TTF studies have shown no negative side effects.

TTF treatment is FDA approved for certain cancer treatments, alone or in conjunction with chemotherapy. However, the current form of TTF has certain limitations. Current TTF therapy is costly, limited in its ability to reach the cancerous growth, and can be difficult to implement. There is a need for improved forms of TTF that can more effectively control the growth of cancer cells.

Pathogenic infections also involve proliferating cells, and these pathogens have the potential to invade or spread to other parts of the body. Pathogenic infections, including those caused by bacteria and fungi are caused by microorganisms that are rapidly dividing. Additionally, viral infections may induce cellular proliferation in infected cells during viral replication and production of infectious progeny. Because pathogenic infections involve proliferating cells, these infections may also be amenable to TTF therapy and its targeted focus on dividing cells.

Although modern medicine has provided treatments and cures for many pathogenic infections, recurring and newly emerging diseases result in enormous annual costs for treatment, and generally require years of studies and trials to develop effective therapeutics and/or preventative vaccines. The current COVID-19 pandemic highlights the necessity for novel treatments that can be rapidly deployed to treat an emerging infectious disease. A recent study indicated that a single symptomatic COVID-19 case could incur a median direct medical cost of $3,045 during the course of the infection, and a single hospitalization case could have a median cost of $14,366. It is estimated that the current COVID-19 pandemic has cost billions of dollars in direct medical expenses alone already, not including the indirect economic costs associated with the pandemic.

With no FDA-approved treatments or vaccines to treat COVID-19 or other newly emerging diseases, medical costs will continue to rise. Further, the hundreds of millions of dollars spent in research and development may only produce a therapeutic that functions against a single pathogen and would not be effective for other emerging or prevalent diseases. Thus, there is an urgent need for novel treatments that can broadly treat and protect against pathogenic infections and the global pandemics that they can cause.

SUMMARY

Controlling and manipulating higher frequencies of alternating current (AC current) has been a centuries old problem. If there were a method of introducing an AC current in TTF with much greater penetration and propagation, then this could be a groundbreaking achievement.

The present disclosure provides a lower cost alternative to existing TTF treatments and makes a significant improvement over existing technologies by applying a frequency that results in significantly greater cytotoxicity to cancer cells. The disclosure includes a considerably more efficient method of inducing a pulsating, modulating AC current with higher penetration resulting in a greater voltage being applied to the targeted tumor or cancer cells. The method and apparatus disclosed herein makes better use of AC current supplied by a battery, for example, due to the improved transmission of AC current electromagnetic signals with less attenuation compared to other systems and apparatuses that are commercially available.

In certain aspects, the present disclosure provides a method of inhibiting the growth of proliferating cells or viruses in living tissue, the method comprising: applying mid-level frequency AC current electromagnetic signals to the living tissue with a transducer comprising a magnetically conductive material passing through a conduction ring energized by an electrical signal to create the mid-level frequency AC current electromagnetic signals within the living tissue; wherein the mid-level frequency AC current electromagnetic signals are produced with an AC voltage generator and have a mid-level frequency in the range of about 50 kHz to about 300 kHz with a modulating amplitude, frequency and random pulse duration to create a decaying sine wave; and circulating fluid in the living tissue provides a secondary coil for the transmission of the mid-level frequency AC current electromagnetic signals. In some embodiments, the mid-level frequency may be modulated using a frequency modulator that adjusts the mid-level frequency AC current electromagnetic signal based on the specific organism or cell type that treatment is designed for. This unique morphology of the AC current provides much better direction, penetration, and reduced attenuation.

In one aspect, the transducer's conduction ring portion extends around the living tissue or some portion thereof. In another aspect, the living tissue is a human body and the transducer's conduction ring extends around an abdomen, a head, an arm, or a leg. In yet another aspect, the conduction ring is composed of a more flexible material that can wrap around the living tissue.

In some embodiments, the circulating fluid in the living tissue is blood, lymph, fluid from nervous or other tissue (e.g., cerebrospinal fluid), or a combination thereof.

In one embodiment, the magnetically conductive material comprises ferrite or other highly conductive material. In another embodiment the highly conductive material is flexible so that it can wrap around a living tissue. In yet another embodiment, the transducer further comprises at least one wire (secondary coil) optionally connected to a resistor; and the at least one wire passes through the conduction ring (forming a secondary coil) and is connected to the living tissue. In another embodiment, the resistor is connected to one end of the wire so as to push the electrical current towards the body. These functions can be with the wire only. The body only or the wire and the body are, in effect, acting as the secondary coil to the transducer.

In another embodiment, the at least one wire is connected to the conduction ring, is looped around the conduction ring at least once, or both. The wire may be looped around the conduction ring two times, three times, four times, five times, or more.

In some aspects, the at least one wire is connected to the living tissue transcutaneously. In one aspect, the at least one wire is connected to the living tissue with Transcutaneous Electrical Nerve Stimulation (TENS) pads or TENS-like pads.

In other aspects, the transducer comprises at least two wires; and the at least two wires are connected to the living tissue at positions rotated 90 degrees angles from each other around the vertical axis of a body.

In some aspects, the one or more wires may be attached to the living tissue in tandem with the conduction ring that extends around or wraps around the living tissue.

In other aspects, the at least one wire is connected to the intravenous (IV) fluid therapy unit that is directly connected to the circulatory system in a subject. In one aspect, the tube of an IV fluid therapy unit is looped around the conduction ring at least once. The tube may be looped around the conduction ring two times, three times, four times, five times, or more.

In certain embodiments, the proliferating cells are cancer cells in a tumor and the at least one wire is connected to the living tissue at a site within 5 cm, 10 cm, 15 cm, 20 cm, or 25 cm from the tumor. In one embodiment, the at least one wire is connected to the living tissue at a site within 25 cm from the tumor.

In some embodiments, the proliferating cells are cancer cells. In other embodiments, the abnormally proliferating cells are bacterial cells, fungal cells, viruses, or archaebacteria. The bacterial cells, viruses, archaebacteria or fungal cells may be, but are not limited to, *Listeria monocytogenes, Pseudomonas* sp., *Serratia marcescens, Clostridium difficile, Staphylococcus aureus, Staphylococcus* sp., *Acinetobacter* spp., *Enterococcus* sp., *Enterobacter* sp., *Escherichia coli, Klebsiella* sp., *Streptococcus* sp., *Haemophilus influenza, Neisseria meningitides*, and *Candida* sp.

In some embodiments, the virus is human immunodeficiency virus, cytomegalovirus, adenovirus, coronavirus, rhinovirus, rotavirus, variola virus, herpes simplex virus, hepatitis B virus, hepatitis A virus, hepatitis C virus, papillomavirus, or *influenza* virus. In a preferred embodiment, the virus is severe acute respiratory syndrome coronavirus 2 (SARS-CoV-2) which causes coronavirus disease 2019 (COVID-19).

In certain aspects, inhibition of the growth of the proliferating cells or viruses is not caused by heat. In other aspects, the inhibition of the growth of the proliferating cells or viruses affects metabolism in the cells.

In other embodiments, the present disclosure is directed to an apparatus for inhibiting the growth of proliferating cells or viruses in living tissue, the apparatus comprising: a transducer comprising a magnetically conductive material passing through a conduction ring energized by an electrical signal to create mid-level frequency AC current electromagnetic signals within the living tissue; an AC voltage generator connected to the transducer to produce the electrical signal; and at least one wire optionally connected to a resistor and passing through the conduction ring of the transducer, wherein the at least one wire is connected to the living tissue or may be connected to an IV fluid therapy unit.

In certain aspects, the transducer is configured to generate mid-level frequency AC current electromagnetic signals in the range of about 50 kHz to about 300 kHz with a modulating amplitude frequency and random pulse duration to create a decaying sine wave. In other aspects, a frequency modulator adjusts the frequency of the signals based on the specific organism or cell type the treatment is being used for.

In other aspects, the magnetically conductive material comprises ferrite. In another aspect the magnetically conductive material comprises a flexible material that can wrap around the living tissue. In one aspect, the resistor has a rheostat. In another aspect, the at least one wire comprises Transcutaneous Electrical Nerve Stimulation (TENS) pads or TENS-like pads to facilitate attachment to the living tissue.

BRIEF DESCRIPTION OF THE DRAWINGS

In FIG. 1A the conductive ring comprises a rigid magnetic material that the living tissue passes through to act as a secondary coil. In these configurations, flexible material has been included to provide padding for the patient and increase comfort for the wearer of the device. In FIG. 1B, a flexible ferrite is used to wrap around the living tissue to act as the secondary coil. Adhesive can be used to form the material into a ring that wraps around living tissue.

FIG. 2 depicts the battery pack and a backpack or waistpack to be used with the portable device. Also shown are self-adhesive electrodes and wires which can be used to enhance voltage emission. The electrodes are attached to the patient's body at a location near the tumor or cancer cells to be treated.

FIG. 4A depicts a patient wearing a configuration of the portable device. The conduction ring of the device is wrapped around the upper arm of the patient with a cord connecting the emitting device to a battery powering the device found in the backpack. In FIG. 4B, the conduction ring of the device is in a backpack and wires are looped around the ring and extend from the backpack to connect to living tissue using an adhesive pad.

5A, the transducer with the conduction ring is worn by the patient on one part of the body and the AC current is transmitted through the circulatory system of the body with the body acting as the secondary coil for the transmission of the signal. The implementation in FIG. 5B is similar to that of FIG. 5A with the addition of a resistor attached to a first wire connected to the body at site distant from the tumor and second wire connected at a site close to the cancerous tumor to be treated. The wires pass through the conduction ring of the transducer and are connected to the body with Transcutaneous Electrical Nerve Stimulation (TENS) pads or TENS-like pads. In one aspect, the resistor depicted in FIG. 5B has a rheostat. FIG. 5C is similar to FIG. 5B with the addition of a second transducer and conduction ring to enhance the signal applied to the tumor. A resistor is not shown in FIG. 5C, but a resistor with or without rheostat may be used in this configuration as well. FIG. 5D depicts an implementation where the transducer and conduction ring are completely external to the body with the wires connected to the body acting as the secondary coil and the body "in series" with the wires. In FIG. 5D, the wires may be connected to the body via a transcutaneous attachment. In FIG. 5E, the signal is wirelessly transmitted to the receiver that is connected to the conductive ring. The receiver may be placed on any appendage, living tissue or structure on the body, or be attached to it. In FIG. 5A-5D implementations, an external power supply box (AC to AC) is plugged into a mobile rechargeable battery worn in a backpack, shoulder strap, waistpack, or similar carrying device (not shown) and is used as the electrical power source for the transducer and conduction ring.

FIGS. 6A and 6B depict different implementations of the disclosed methods and devices designed to increase the intensity and directionality of the electrical signal produced. In FIG. 6A, the transducer with the conduction ring is worn by the patient on one part of the body (e.g., on the arm or leg). A wire is connected directly to the conduction ring and is then looped around the conduction ring one time, two times, three times, or more with the other end of the wire attached to the body of the patient. In FIG. 6B, the transducer with the conduction ring is not worn by the patient, and the wire is configured as in FIG. 6A with one end attached to the patient's body.

In FIG. 7A, the wire is directly attached to the patients' bodies. In FIG. 7B the ends of the wire can be connected to a conduction ring that passes over the patient's head. One device can be connected to conduction rings on several hospital beds at the same time. The wire may also be directly connected to and wrap around the base of a patient's hospital bed. In FIG. 7C, the wire is directly attached to the patients' bodies after wrapping in opposite directions around the conduction ring. Using any of these methods, multiple patients can be connected to the same device.

In FIG. 8A, the wire is connected to a single IV fluid therapy unit. FIG. 8B depicts one device connected to multiple IV fluid therapy units at the same time. The wire connecting the device to the IV fluid therapy unit may or may not be wrapped around a conduction ring. FIG. 8C depicts how one device may directly connect to IV fluid therapy units by the wire, and how the IV connection tube may wrap around the conduction ring before being connected to the patient to feed into the circulatory system of the patient. In FIG. 8D, multiple devices are directly connected to several IV fluid therapy units by the wire, and the IV tubes wrap around the device's conduction ring before connecting to the patient to feed into the patient's circulatory system. In FIG. 8E, the wire is split, wrapping around the conduction ring in opposite directions before connecting to different IV fluid therapy units.

FIGS. 9A, 9B, 9C, and 9D depict two different implementations of the disclosed methods. FIG. 9A depicts an implementation wherein the wire is connected directly to an individual by a TENS pad or TENS-like pad and wherein the device is powered by an electrical source using a grounded plug. FIG. 9B illustrates how the wire can be directly connected to an individual, wherein the wire is looped at least once around a conduction ring that surrounds living tissue. The device is grounded using a grounded plug. FIGS. 9C and 9D depict the implementations of FIGS. 9A and 9B having a split wire wrapping in opposite directions around the conduction ring before attaching to two locations on the patient's body.

FIG. 10B depicts how the conductive metal ring can surround living tissue in the subject and the at least one wire is connected to a grounding mat or sheet and the other end of the wire is grounded using a grounded plug. FIG. 10C depicts the device receiving power from an electrical outlet separate from the grounded plug connected to the grounding mat or sheet. FIGS. 10D-10F depict the implementations of FIGS. 10A-10C, respectively, having a split ground wire wrapping in opposite directions around the conduction ring before connecting to the same grounding device.

DETAILED DESCRIPTION

Figure 1A:
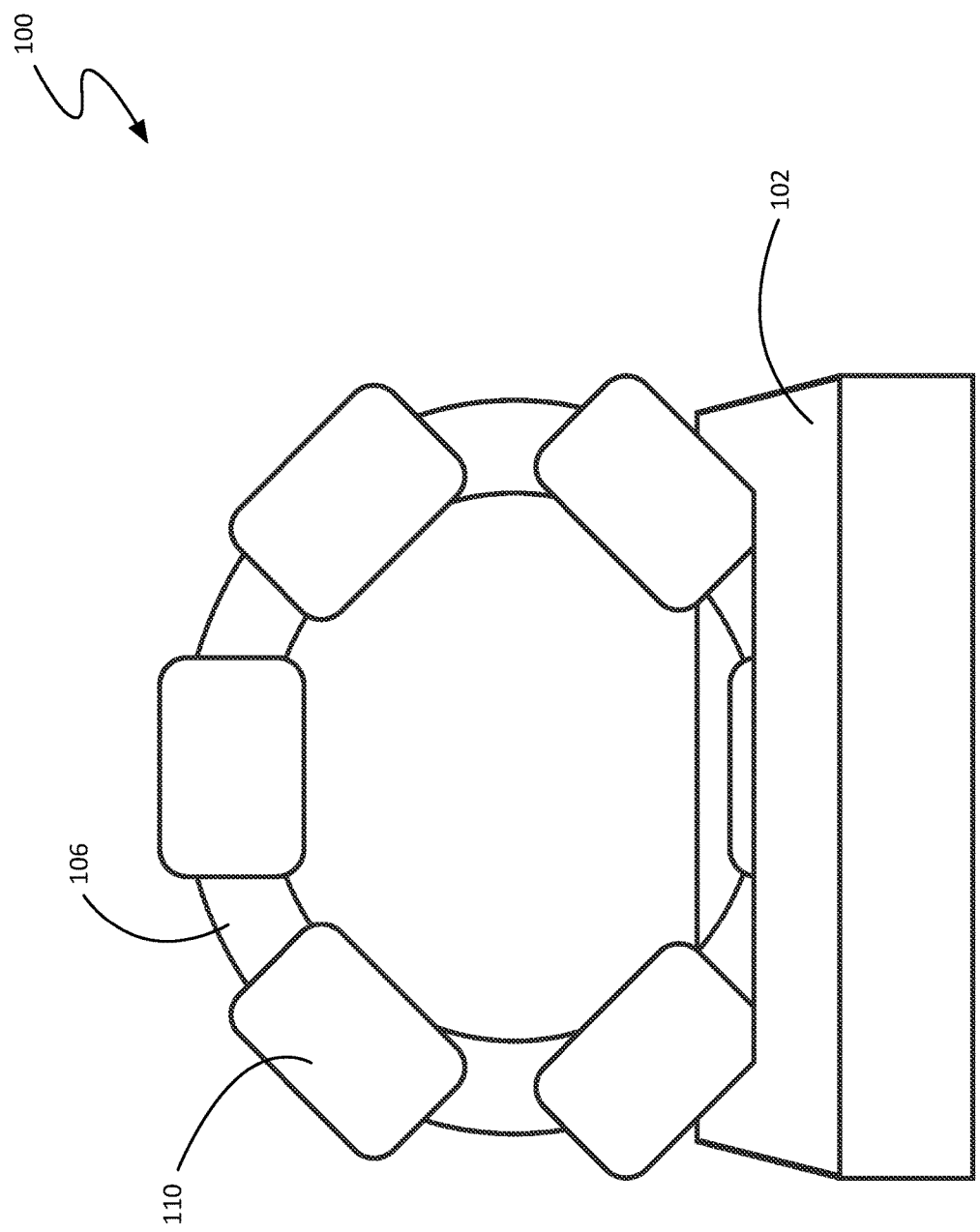
FIGS. 1A, and 1B depict alternative configurations of the portable device emitting a specialized AC current that makes its wearer (i.e., the patient) the secondary coil to complete the system.

As used herein and in the appended claims, the singular forms "a," "an," and "the" include plural referents unless the context clearly dictates otherwise. For example, "a" or "an" means "at least one" or "one or more." Thus, reference to "an antibody or antigen binding fragment thereof refers to one or more antibodies or antigen binding fragments thereof, and reference to "the method" includes reference to equivalent steps and methods disclosed herein and/or known to those skilled in the art, and so forth.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

A "subject" as used herein refers to an organism, or a part or component of the organism, to which the provided methods, apparatuses, and systems can be administered or applied. For example, the subject can be a mammal or a cell, a tissue, an organ, or a part of the mammal. Mammals include, but are not limited to, humans, and non-human animals, including farm animals, sport animals, rodents, and pets.

Living organisms proliferate by cell division, including tissues, cell cultures, microorganisms (such as bacteria, *mycoplasma*, yeast, protozoa, and other single-celled organisms), fungi, algae, plant cells, etc. Viruses may infect cells that are in the process of cell division or induce cells to undergo cell division in order to produce new virus progeny. When in the process of dividing, cells of organisms can be destroyed, or their proliferation controlled, by methods that are based on the sensitivity of the dividing cells of these organisms to certain chemical or physical agents.

It is well known that tumors, particularly malignant or cancerous tumors, grow uncontrollably compared to normal tissue. Such expedited growth enables tumors to occupy an ever-increasing space and to damage or destroy tissues and organs adjacent thereto. Furthermore, certain cancers are characterized by an ability to spread metastases to new locations where the metastatic cancer cells grow into additional tumors.

The rapid growth of tumors, in general, and malignant tumors in particular is the result of relatively frequent cell division of these cells compared to normal tissue cells. The distinguishably frequent cell division of cancer cells is the basis for the effectiveness of many existing cancer treatments, e.g., irradiation therapy and the use of various chemo-therapeutic agents. Such treatments are based on the fact that cells undergoing division are more sensitive to radiation and chemo-therapeutic agents than non-dividing cells. Because tumor cells divide much more frequently than normal cells, it is possible, to a certain extent, to selectively damage or destroy tumor cells by radiation therapy and/or chemotherapy. The actual sensitivity of cells to radiation, therapeutic agents, etc., is also dependent on specific characteristics of different types of normal or malignant cells. Unfortunately, in many cases the sensitivity of tumor cells to the applied therapeutic agent is not sufficiently higher than that of many types of normal tissue; therefore, existing cancer treatments typically cause significant damage to normal tissues, thus limiting the therapeutic effectiveness of such treatments. Also, certain types of tumors are not sensitive at all to existing methods of treatment.

It is well appreciated that microorganisms proliferate rapidly throughout the course of infection or stimulate proliferation of living tissue. Such proliferation allows the microorganisms to potentially spread throughout the body and to new hosts. Tissues can be damaged by the microorganisms themselves as they replicate, or by a sustained immune response.

Therapeutics may target microorganisms at multiple stages of the infection cycle, including during replication. Drugs may arrest replication of a microorganisms, inhibit production of necessary materials, or shut down protein production in an infected cell to block pathogen replication. Because these microorganisms have genomic material that is replicated, mutations may occur during the course of infection. Selective pressure from treatment with drugs targeting specific stages of the replication or infection cycle can lead to mutations that subvert a given drug's mechanism of action and efficacy. The rise of drug resistant "superbugs" is evidence of this phenomena, and these pathogens cannot be treated with conventional drugs. Additionally, because many of these drugs target specific microorganisms, when a new infectious microorganism emerges, there are no effective therapeutics that can be used to treat individuals with the infection because of the specificity of existing drugs.

Electric fields and currents have been used for medical purposes for many years. The most common use is the generation of electric currents in a human or animal body by application of an electric field by means of a pair of conductive electrodes between which a potential difference is maintained. These electric currents are used either to exert their specific effects, i.e., to stimulate excitable tissue, or to generate heat by flowing in the body since it acts as a resistor. Examples of the first type of application include the following: cardiac defibrillators, peripheral nerve and muscle stimulators, brain stimulators, etc. Currents are used for heating, for example, in devices for tumor ablation, ablation of malfunctioning cardiac or brain tissue, cauterization, relaxation of muscle rheumatic pain and other pain, etc.

Another use of electric fields for medical purposes involves the utilization of high frequency oscillating fields transmitted from a source that emits an electric wave, such as an RF wave or a microwave source, which is directed at the part of the body that is of interest (i.e., a target).

Historically, electric fields used in medical applications were separated into two types, namely (1) steady fields or fields that change at relatively slow rates, and alternating fields of low frequencies that induce corresponding electric currents in the body or tissues, and (2) high frequency alternating fields (above 1 MHz) applied to the body by means of the conducting electrodes or by means of insulated electrodes.

The first type of electric field has been used, for example, to stimulate nerves and muscles, pace the heart, etc. In fact, such fields are used in nature to propagate signals in nerve and muscle fibers, the central nervous system (CNS), heart, etc. The recording of such natural fields is the basis for the ECG, EEG, EMG, ERG, etc. The field strength in a medium having uniform electric properties is simply the voltage applied to the stimulating/recording electrodes divided by the distance between them. The currents thus generated can be calculated by Ohm's law. Those currents, however, can have dangerous stimulatory effects on the heart and CNS and can result in potentially harmful ion concentration changes. Also, if the currents are strong enough, they can cause excessive heating in the tissues. This heating can be calculated by the power dissipated in the tissue (the product of the voltage and the current).

When such electric fields and currents are alternating, their stimulatory power (e.g., on nerve, muscle, etc.) is an inverse function of the frequency. At frequencies above 10 kHz, the stimulation power of the field approaches zero. This limitation is due to the fact that excitation induced by electric stimulation is normally mediated by membrane potential changes, the rate of which is limited by the resistive and capacitive properties (with time constants on the order of 1 m) of the membrane.

Regardless of the frequency, when such current inducing fields are applied, they are often associated with harmful side effects caused by currents. For example, one negative effect is the change in ionic concentration in the various "compartments" within the system, and the harmful products of the electrolysis.

Historically, alternating fields of medium frequencies (about 50 kHz-1 MHz) were thought not to have any biological effect except due to heating. But more recently, the usefulness of such fields has been recognized, particularly when the fields are applied to a conductive medium, such as a human body, via insulated electrodes. Under such conditions the electrodes induce capacitive currents in the body. In U.S. Pat. Nos. 7,016,725, 7,089,054, 7,333,852, 7,805,201, and 8,244,345 by Palti (each of which is incorporated herein by reference) and in a publication by Kirson (see Eilon D. Kirson, et al., Disruption of Cancer Cell Replication by Alternating Electric Fields, Cancer Res. 2004 64:3288-3295), such fields have been shown to have the capability to specifically affect cancer cells and serve, among other uses, for treating cancer. These fields are often referred to as TTF or TTFields.

TTFields exert directional forces on polar microtubules and interfere with the assembly of the normal mitotic spindle. Such interference with microtubule dynamics results in abnormal spindle formation and subsequent mitotic arrest or delay. Cells can die while in mitotic arrest or progress to cell division. This can lead to the formation of either normal or abnormal aneuploid progeny. The formation of the tetraploid cells can occur either due to mitotic exit through slippage or can occur during improper cell division. Abnormal daughter cells can die in the subsequent interphase, can undergo a permanent arrest, or can proliferate through additional mitosis where they will be subjected to further TTFields assault. See M. GILADI et al. Mitotic Spindle Disruption by Alternating Electric Fields Leads to Improper Chromosome Segregation and Mitotic Catastrophe in Cancer Cells, Scientific Reports, 2015; 5:18046. Different cell types and/or organisms will exhibit different peak cytotoxic frequencies (PCF), that is, the frequency that exhibits the greatest cytotoxic effect on the target cell or organism.

In certain aspects, the present disclosure provides a portable device 100 comprising a transducer 102 that emits a specialized AC current and makes its user 104 the secondary coil to complete the circuit. Examples of similar devices and methods to use such devices are described in U.S. Pat. Nos. 5,514,283; 5,667,677; 9,032,610, 9,140,412; 4,863,344; 5,935,433; 8,029,669; 8,033,334; 8,168,059; 8,231,786; 9,032,610; and 9,140,412, each of which is incorporated by reference.

Figure 1B:
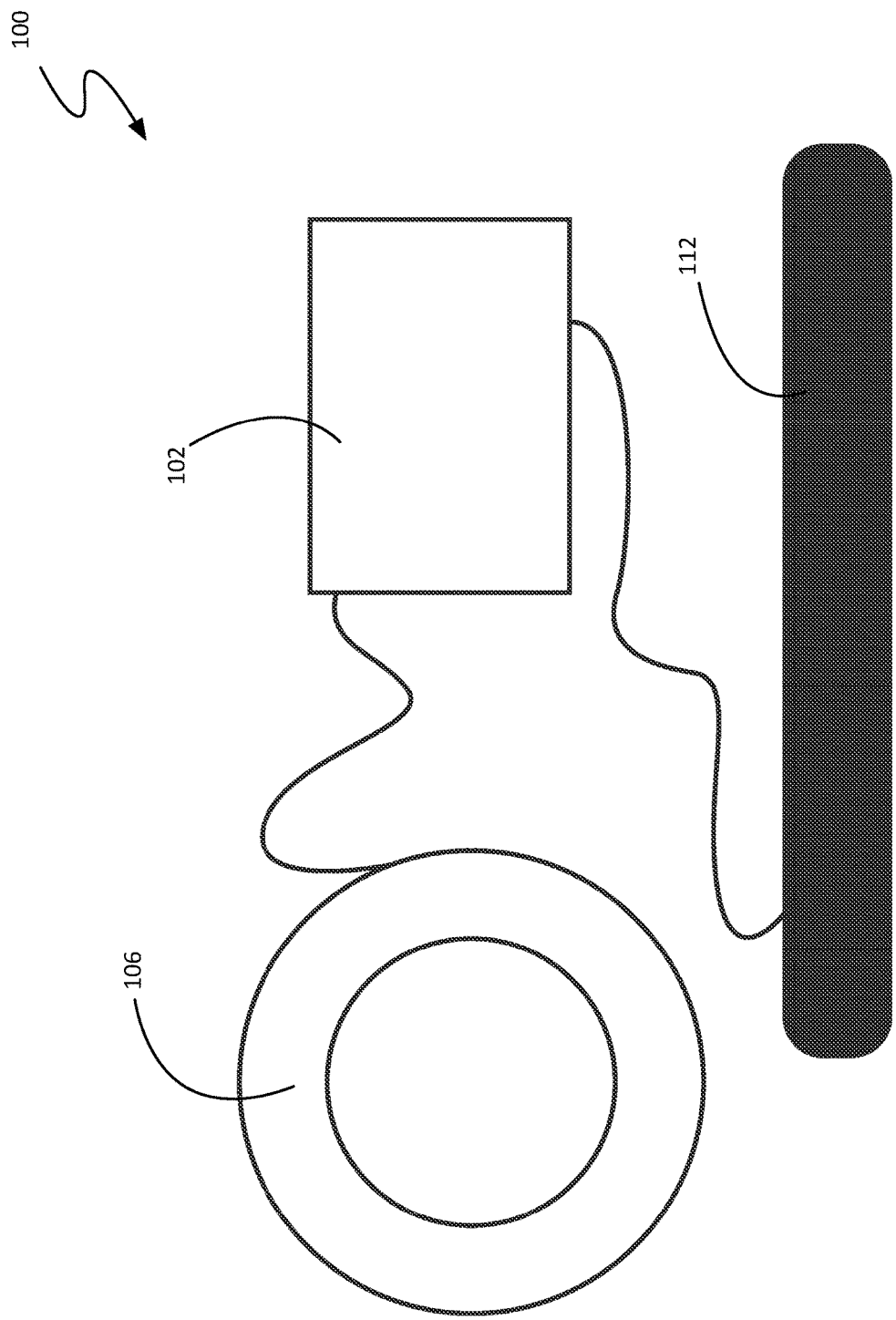
Figure 3:
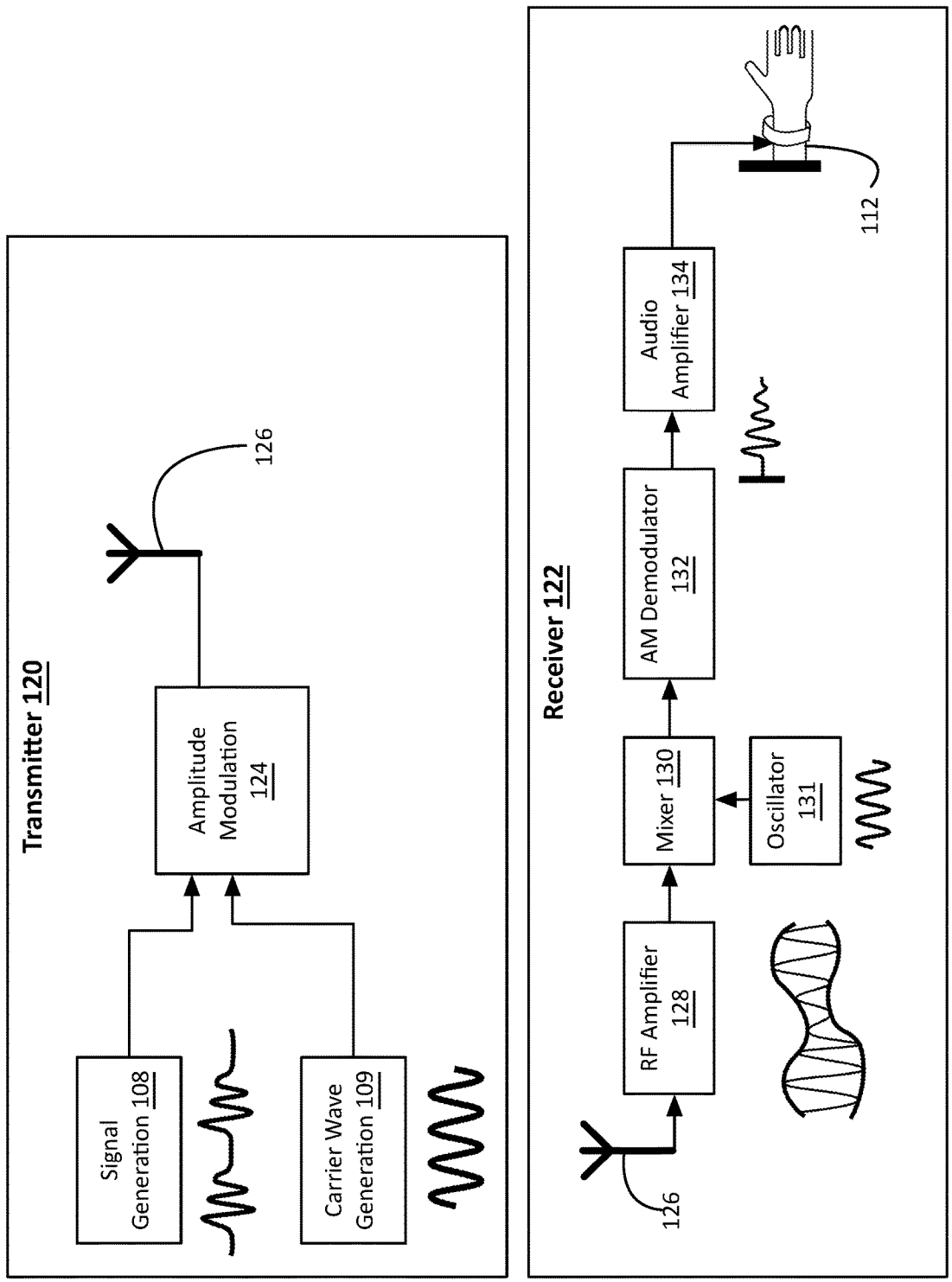
FIG. 3 depicts a wireless configuration of the portable device. A signal is generated, and the amplitude may be modulated prior to transmission through an antenna. The signal is received through an antenna on the receiver. The signal is then processed through a mixer, a demodulator, and an amplifier before the output signal is produced and transmitted to the conductive ring.

As shown in FIG. 1A, the transducer 102 comprises a magnetically conductive material which passes through a conduction ring 106. The conduction ring 106 is energized by an electrical signal generated by an AC voltage generator 108 (see FIG. 3). The conduction ring 106 may be rigid and may include padding 110 to make the conduction ring 106 more comfortable to the user 104. As shown in FIG. 1B, the conduction ring 106 may be coupled with a flexible ferrite 112.

FIG. 2 illustrates a battery 114 which may be used to power the portable device 100. Additionally, portable device 100 may comprise at least one wire 116 and an electrode 118 to carry the electrical signal to a location near the cells to be treated. In one aspect illustrated in FIGS. 3 and 5E, a signal transmitter 120 communicates the signal wirelessly with a receiver 122 to produce the specialized AC current in the conduction ring 106. The signal is initially generated and amplified by an amplifier 124. The signal is then transmitted from the transmitter 120 through an antenna 126. The signal is received by the receiver 122 that directs the signal to an amplifier 128 and mixer 130. The amplifier 128 and mixer 130 then transmit the signal to a demodulator 132. The demodulator 132 processes the signal, and the signal is then transmitted to an audio amplifier 134 that produces the final output signal that is then transmitted to the conduction ring 106.

Figure 4A:
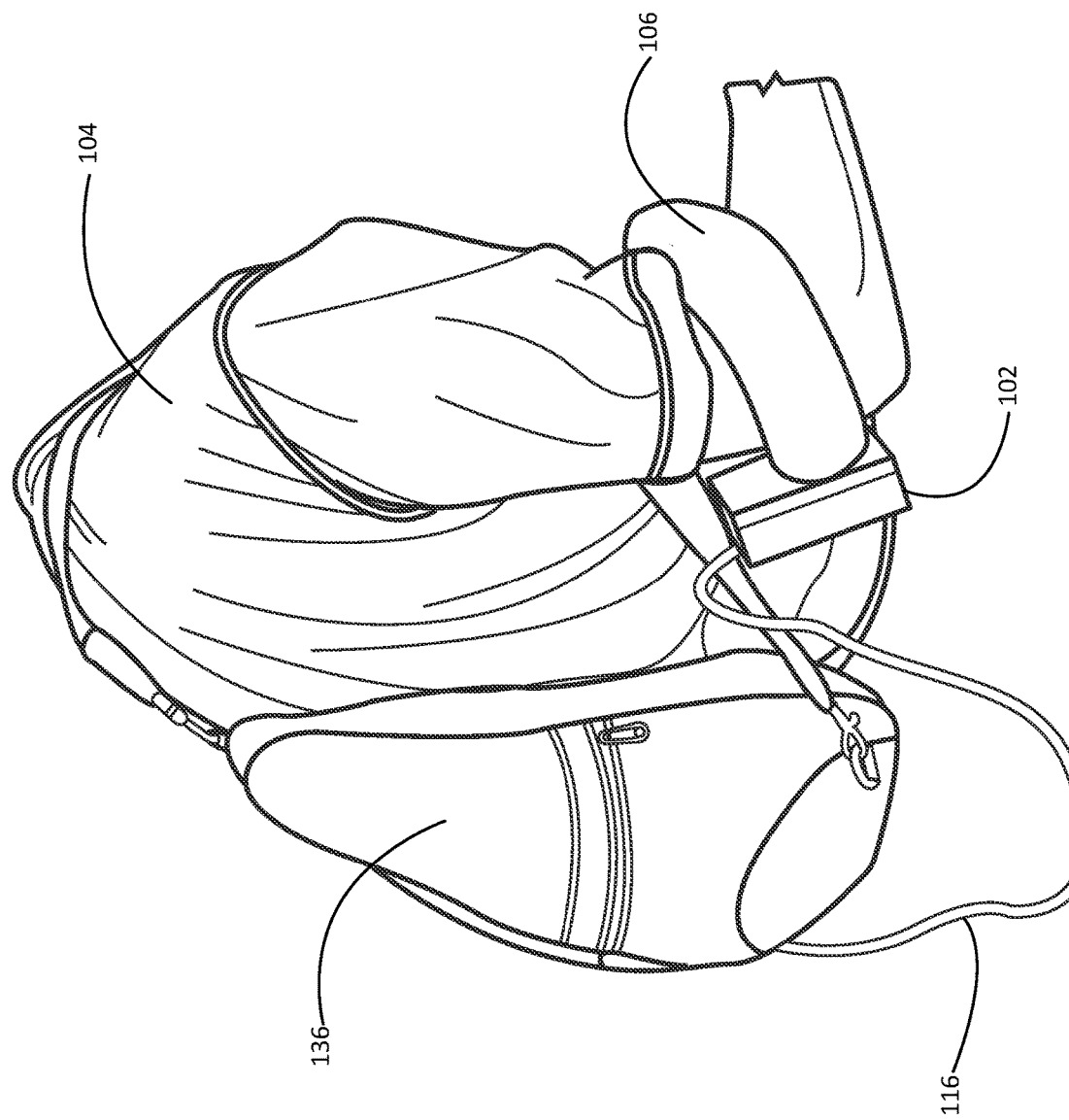
FIGS. 4A and 4B depict portable configurations of the device.
Figure 4B:

In certain aspects illustrated in FIGS. 2 and 4A-4B, the portable device further comprises the battery 114 and a backpack 136 with a wire 116 connecting the battery 114 to the transducer 102. The backpack 136 may be used to carry the portable device 100. In such an embodiment, the conduction ring 106 may be worn by the user 104 (see FIG. 4A), or the conduction ring 106 may be carried in the backpack 136 (see FIG. 4B). If the conduction ring 106 is carried in the backpack 136, the conduction ring 106 may be connected to the user 104 through a wire 116 and an adhesive pad 138. The adhesive pad 138 may be a Transcutaneous Electrical Nerve Stimulation (TENS) pad.

In another aspect, the signal is generated and is transmitted through a wire 116 to the conductive metal ring.

In one aspect, the signal is a mid-level frequency AC current from (80 to 250 KHz) that has a modulating amplitude frequency and random duration. In another aspect, the signal may be modulated by a frequency modulator to adjust the mid-level frequency AC current based on the target's PCF before the signal is transmitted to the conductive metal ring.

The signal propagates throughout the body's vasculature and lymphatic system and the AC current has a cytotoxic effect on cancer cells and pathogenic microbes as well as improves nutrient uptake as well as other symptoms of cancer treatment. In certain aspects, the method improves symptoms associated with irritable bowel syndrome (IBS).

Figure 5A:
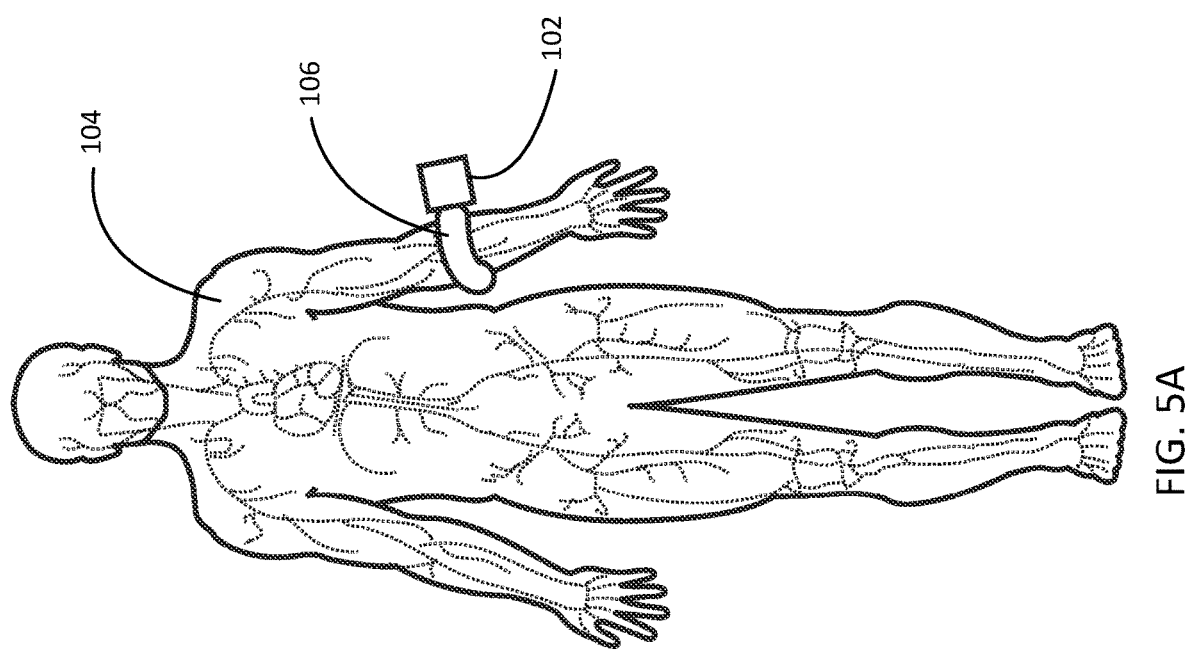
FIGS. 5A, 5B, 5C, 5D, and 5E depict different implementations of the disclosed methods and devices. In FIG.

As shown in FIGS. 5A-5E, in certain aspects, the method for transmitting the field is twofold:

Primary Method of Transmission—The conduction ring 106 is wrapped around an appendage or trunk of the user 104, as shown in FIG. 5A. This turns the actual body of the user 104 into the secondary coil of the System.

Figure 5B:
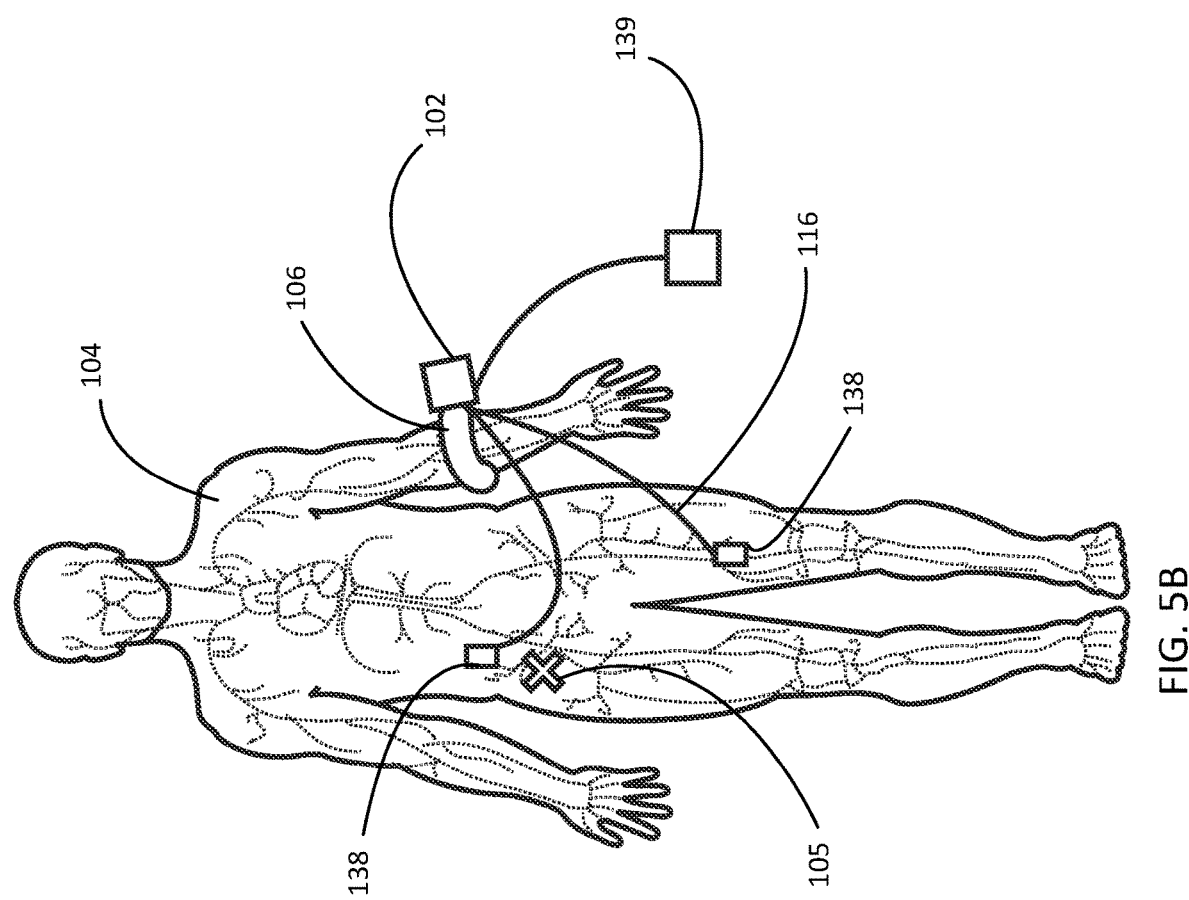
Figure 5C:
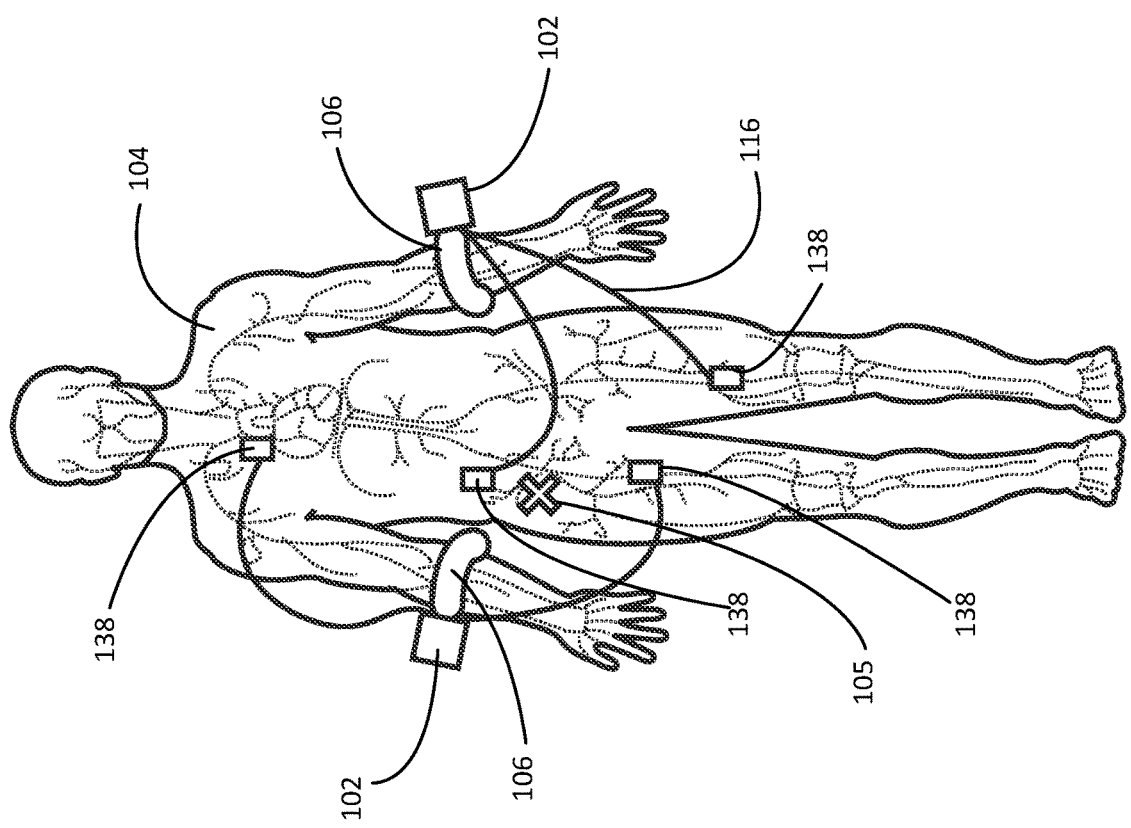
Figure 5D:
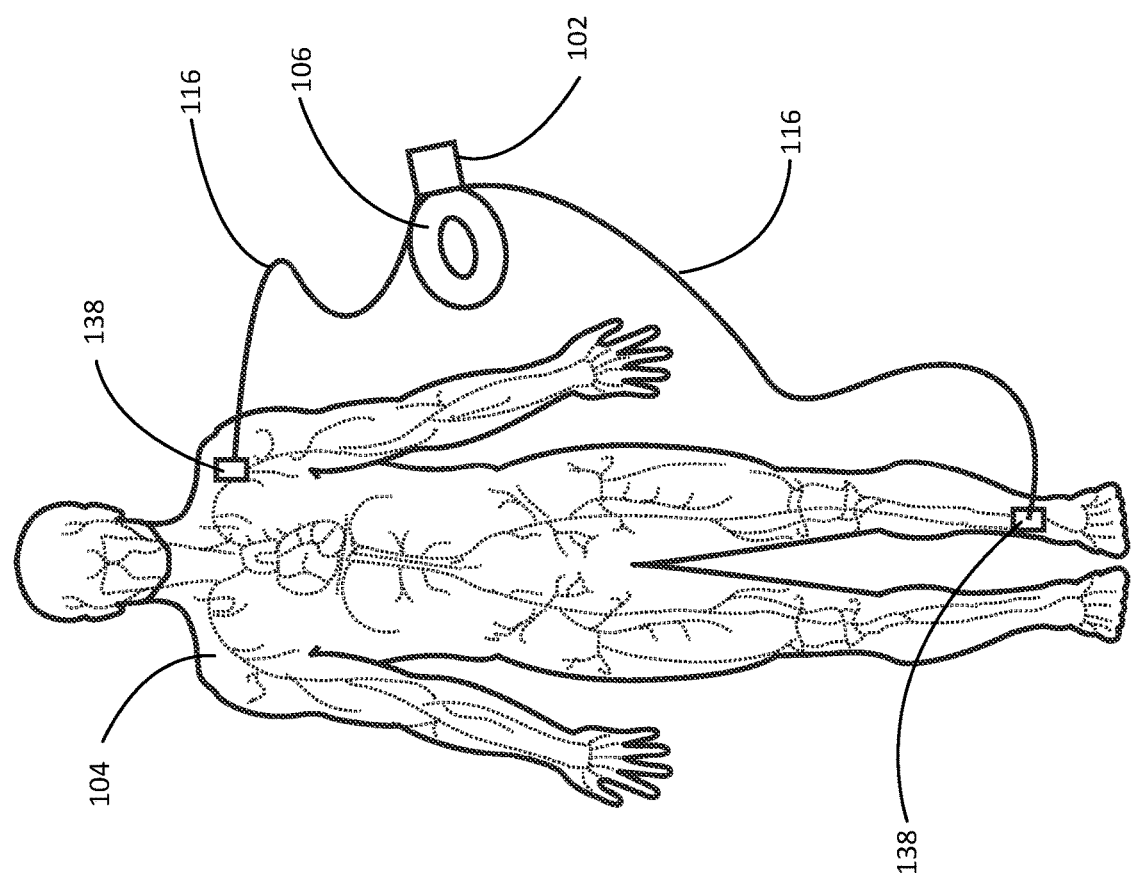
Figure 5E:
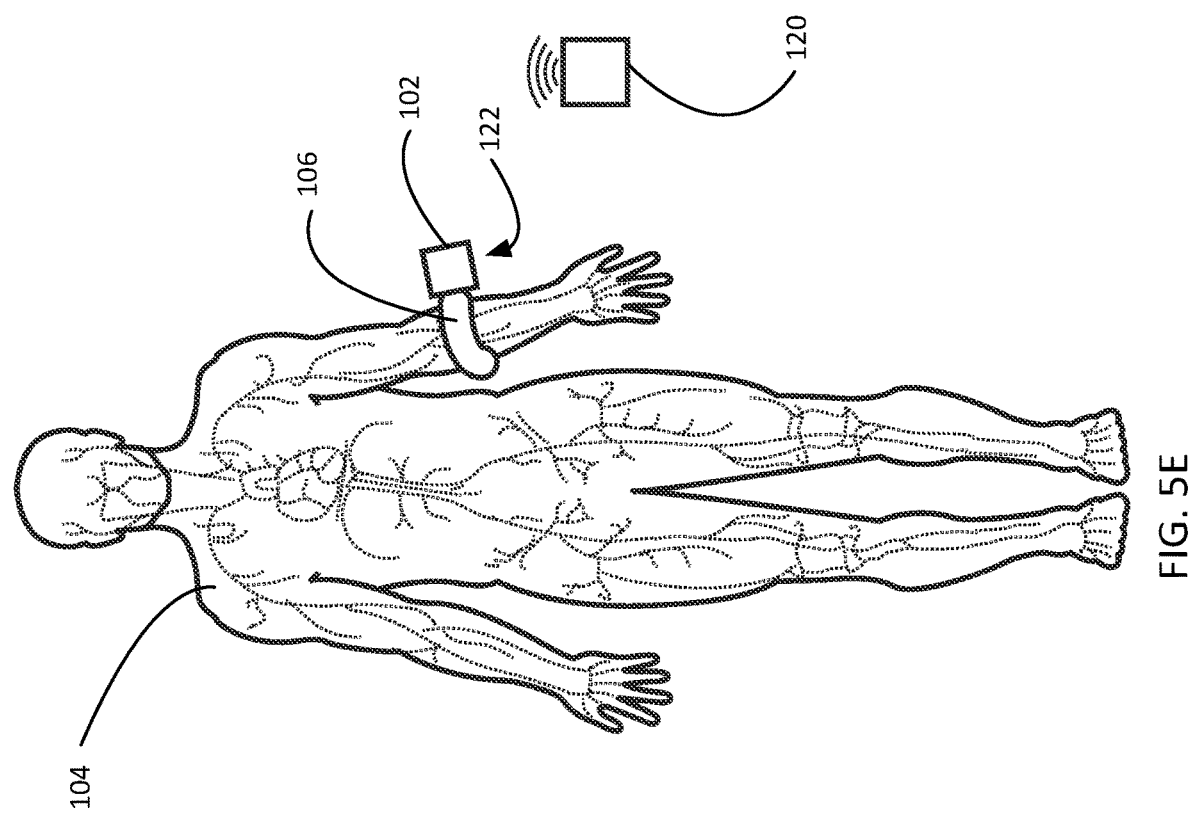

Secondary Method of Transmission—There are also one or more wires 116 that are passed through the conduction ring 106 and are placed with TENS or TENS-like attachment pads 138 placed strategically around the tumor area 105 or elsewhere on the body of the user 104, as shown in FIGS. 5B-5D that enhance the existing signal that is already propagating throughout the body. The one or more wires 116 can be wrapped around the conduction ring 106 once or many times to enhance voltage emission. These wires 116 can be used with the portable device 100 attached to the body or with the portable device 100 placed externally to the body. In some embodiments, including the non-limiting example shown in FIG. 5B, a resistor 139 may be attached to a first wire connected to the body at a site distant from the tumor and a second wire connected at a site close to the cancerous tumor. In some embodiments, this resistor 139 may be a rheostat.

In addition to being directly connected to the body, the one or more wires 116 may alternatively be connected to an intravenous (IV) therapy fluid unit 140 that is directly connected to the circulatory system (see FIGS. 8A-8D). The one or more wires 116 may also be connected to the living tissue or IV therapy fluid unit 140 in tandem with the conduction ring 106 wrapping around living tissue on the user 104, as illustrated in FIG. 5C. In addition, the conduction ring 106 may not be wrapped around an appendage or trunk of the user 104, and instead may only be connected to the user 104 through the one or more wires 116, as illustrated in FIG. 5D.

Figure 6A:
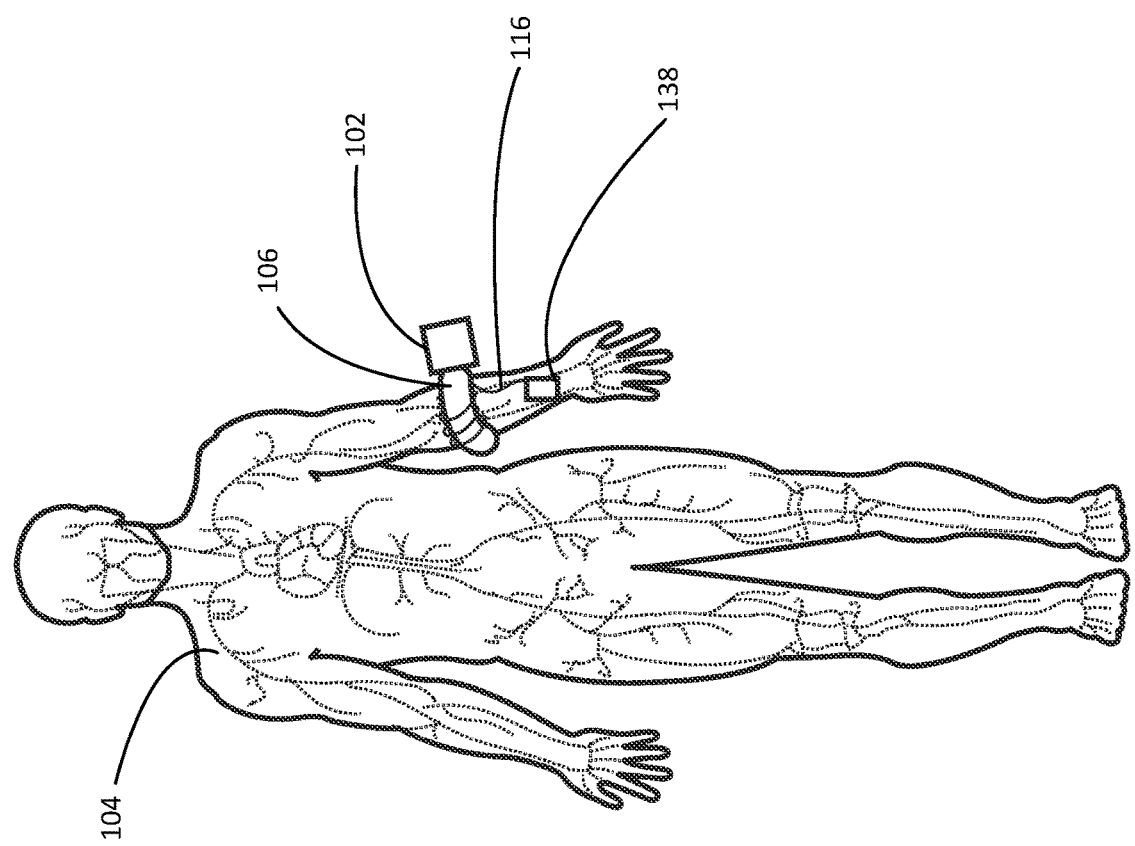
Figure 7A:
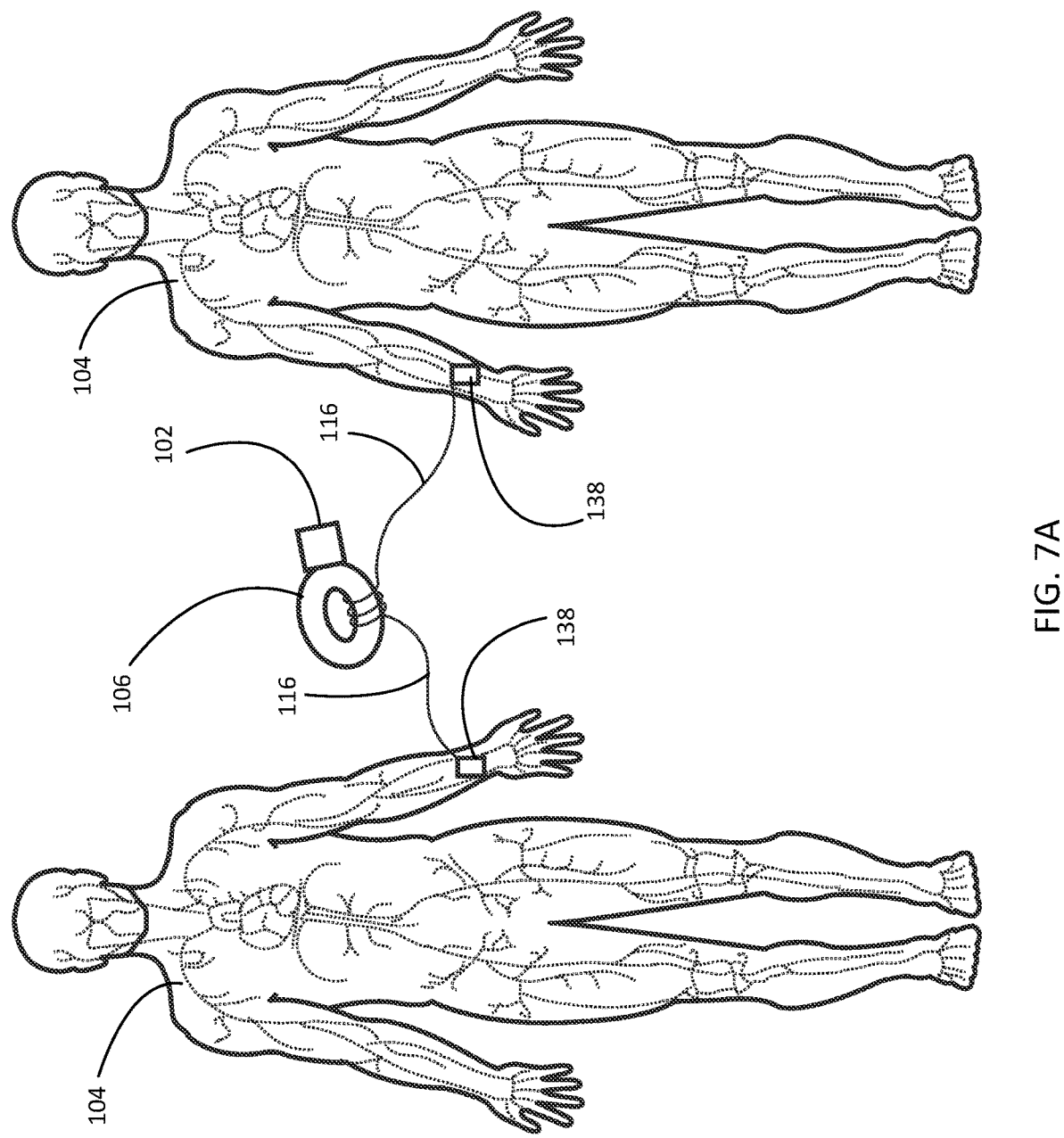
FIGS. 7A, 7B, and 7C depict different implementations of the disclosed methods and devices wherein the wire loops around the conduction ring with the wire's ends connected to at least two different patients.
Figure 7B:
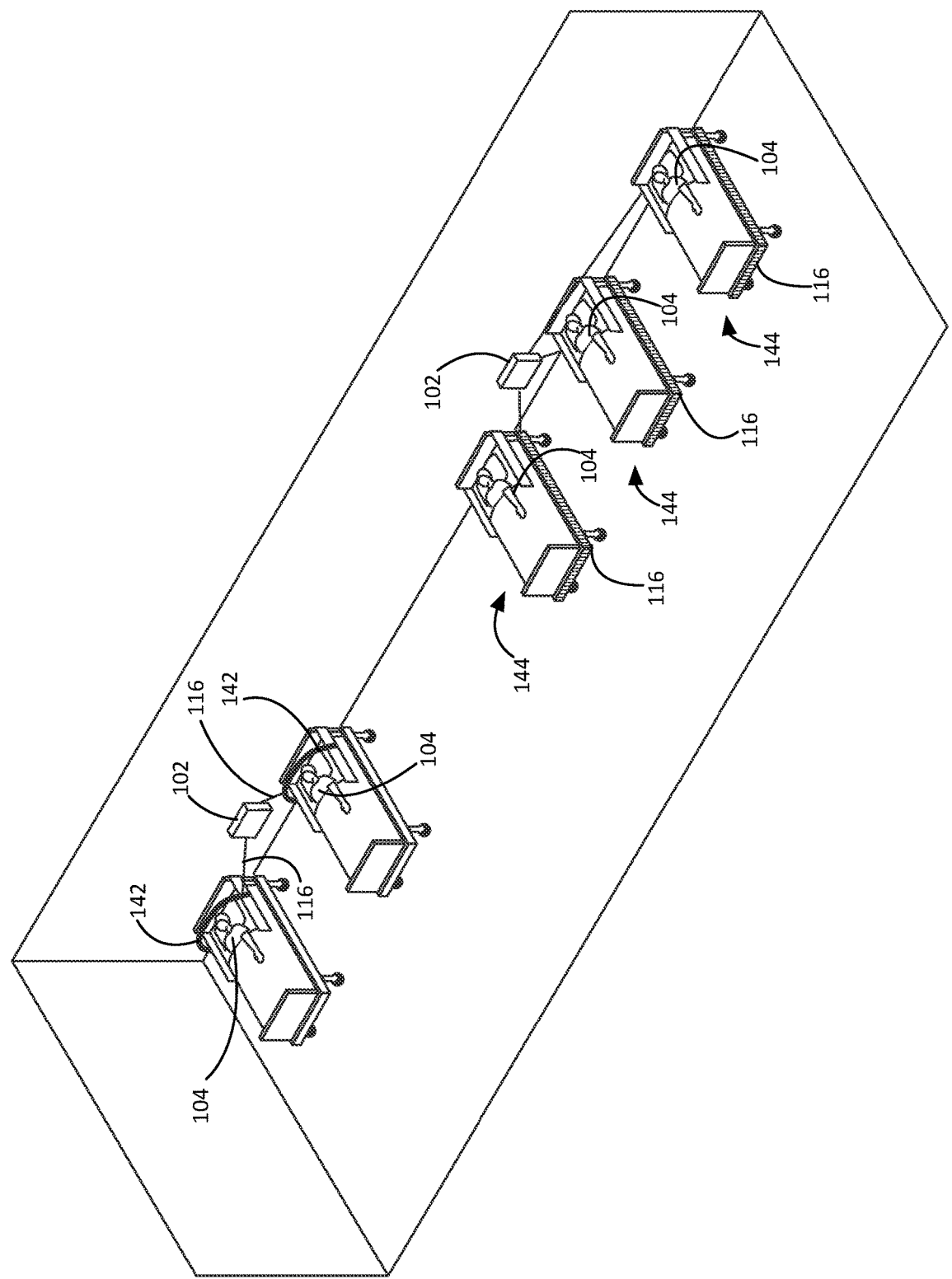
Figure 7C:
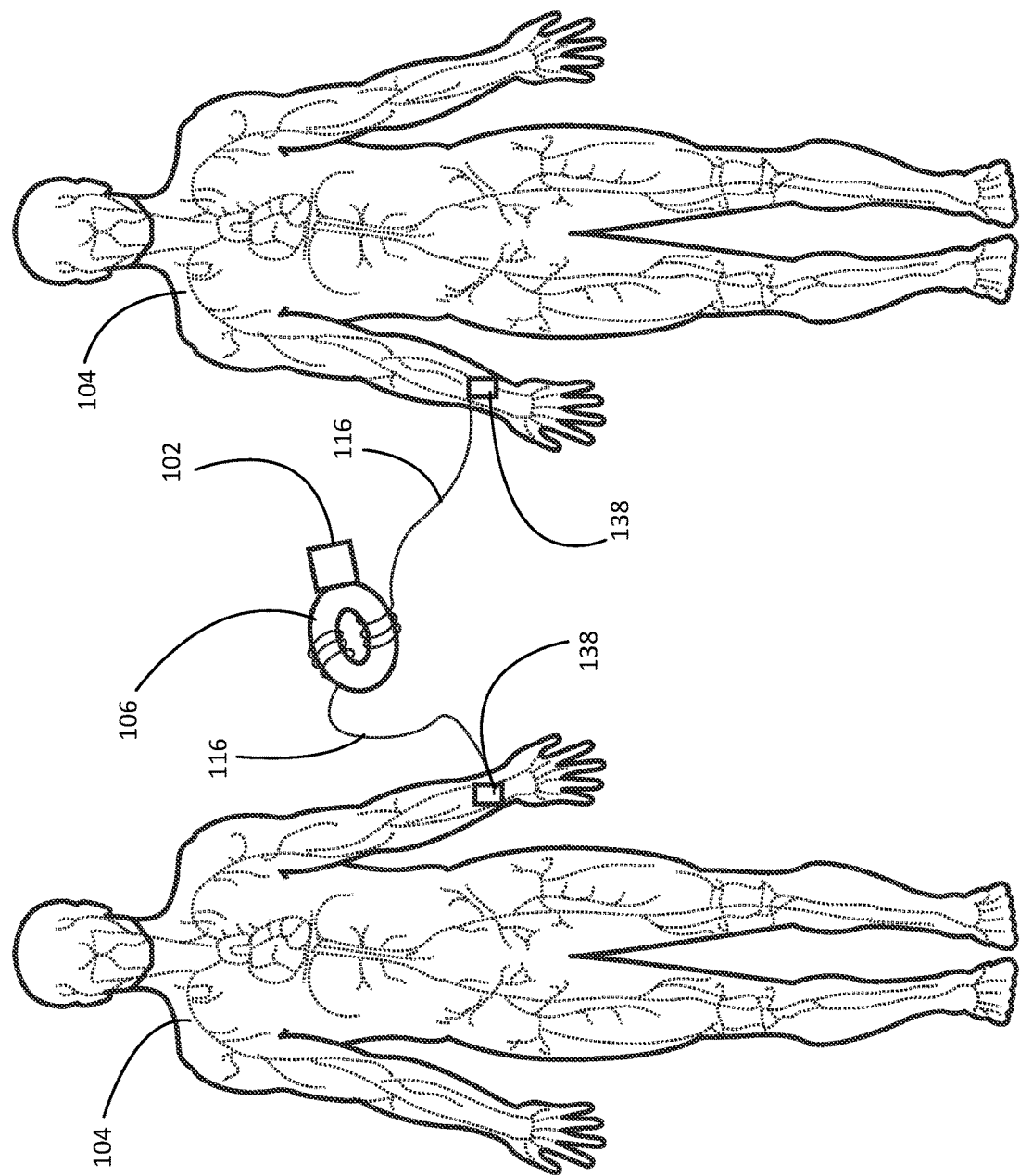
Figure 8A:
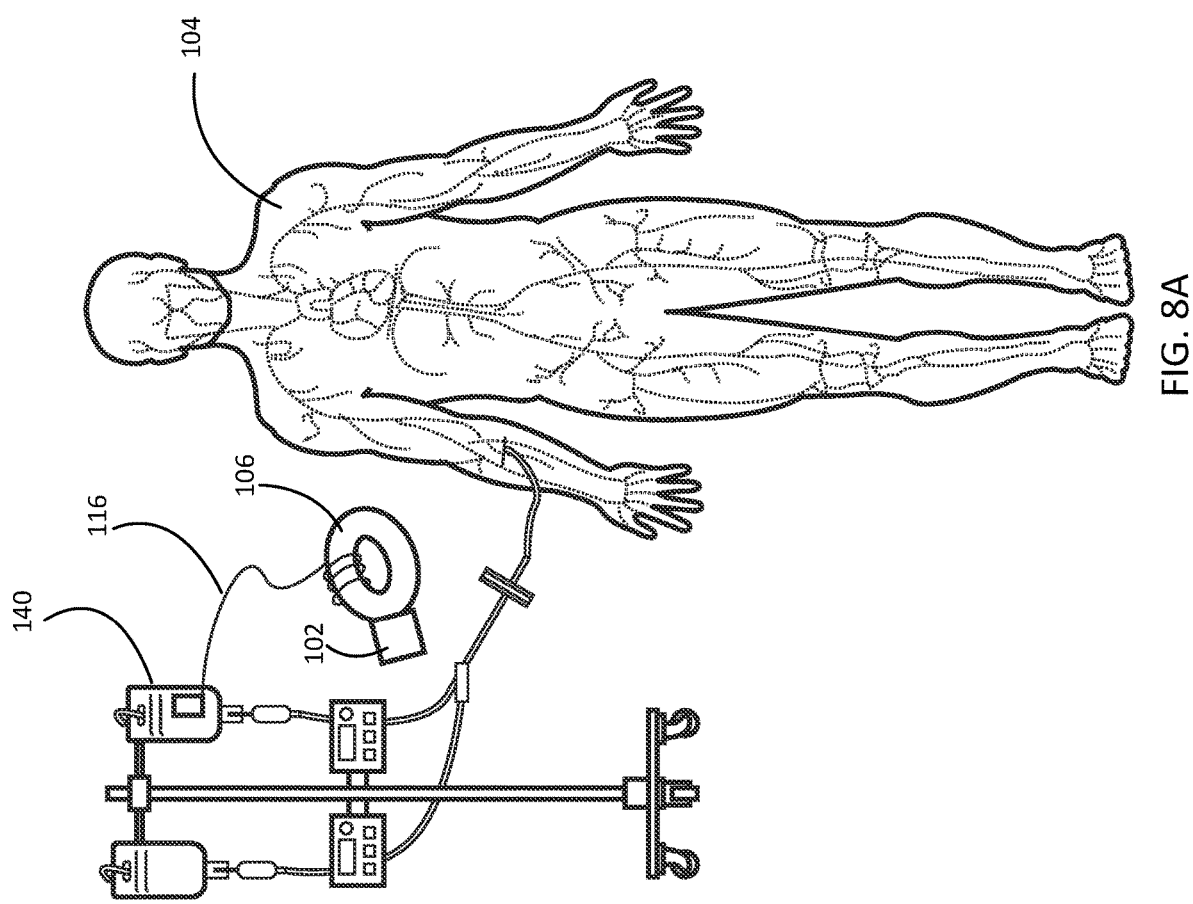
FIGS. 8A, 8B, 8C, 8D, and 8E depict different implementations of the disclosed methods and devices wherein the wire is connected to and loops around the conduction ring with the other end of the wire connected to an IV fluid therapy unit feeding into the circulatory system of the patient.
Figure 8B:
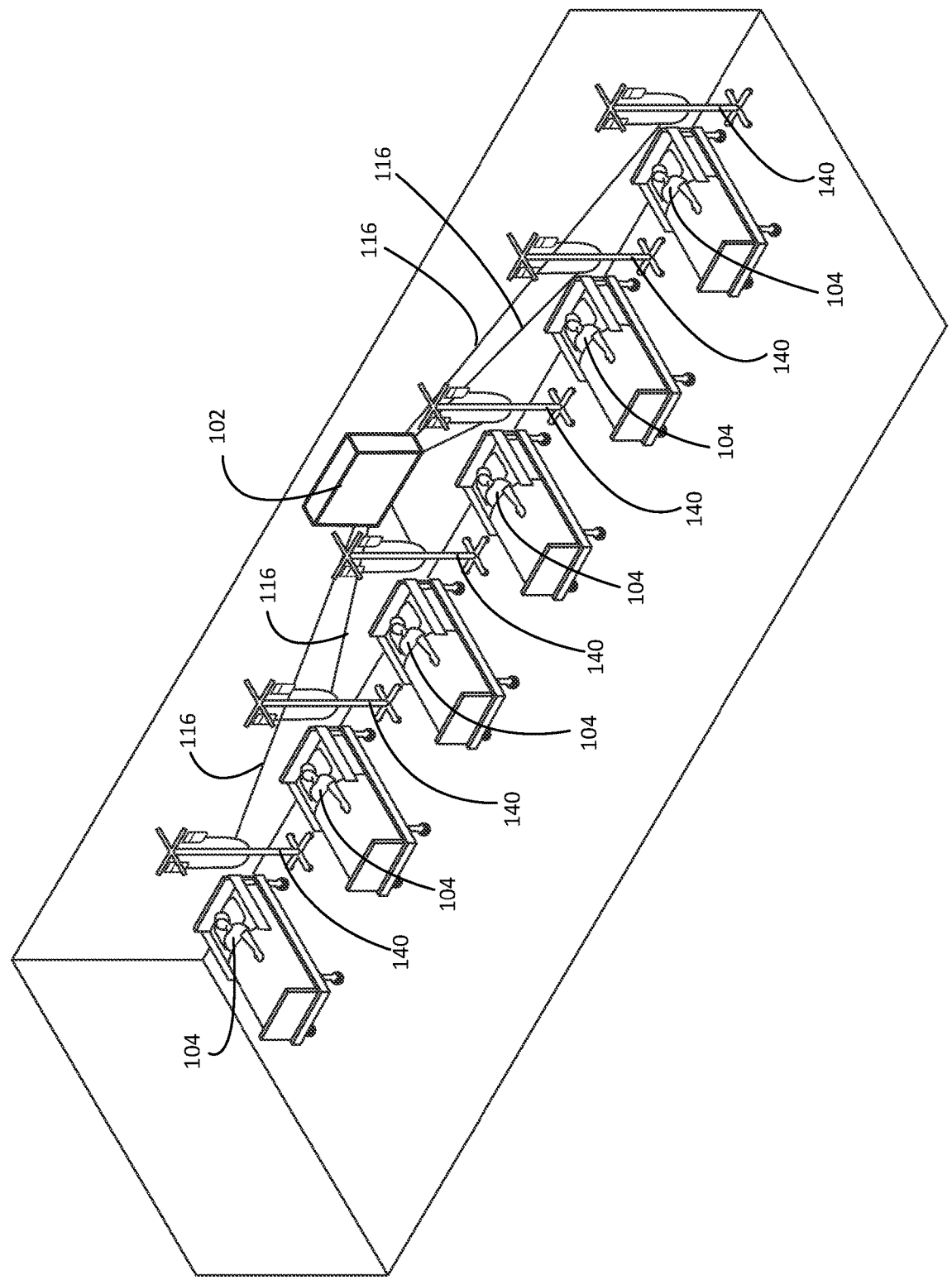
Figure 8C:
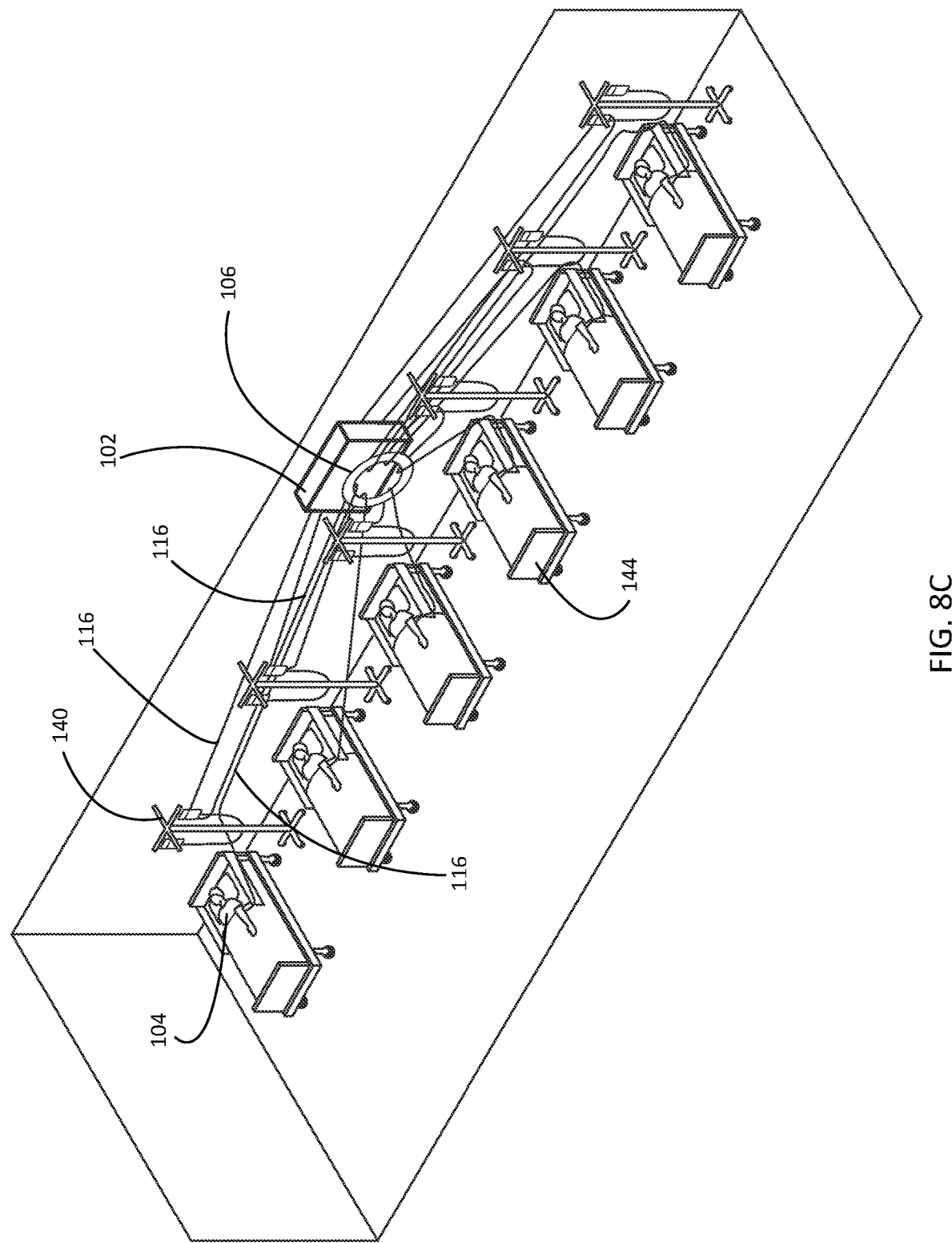
Figure 8D:
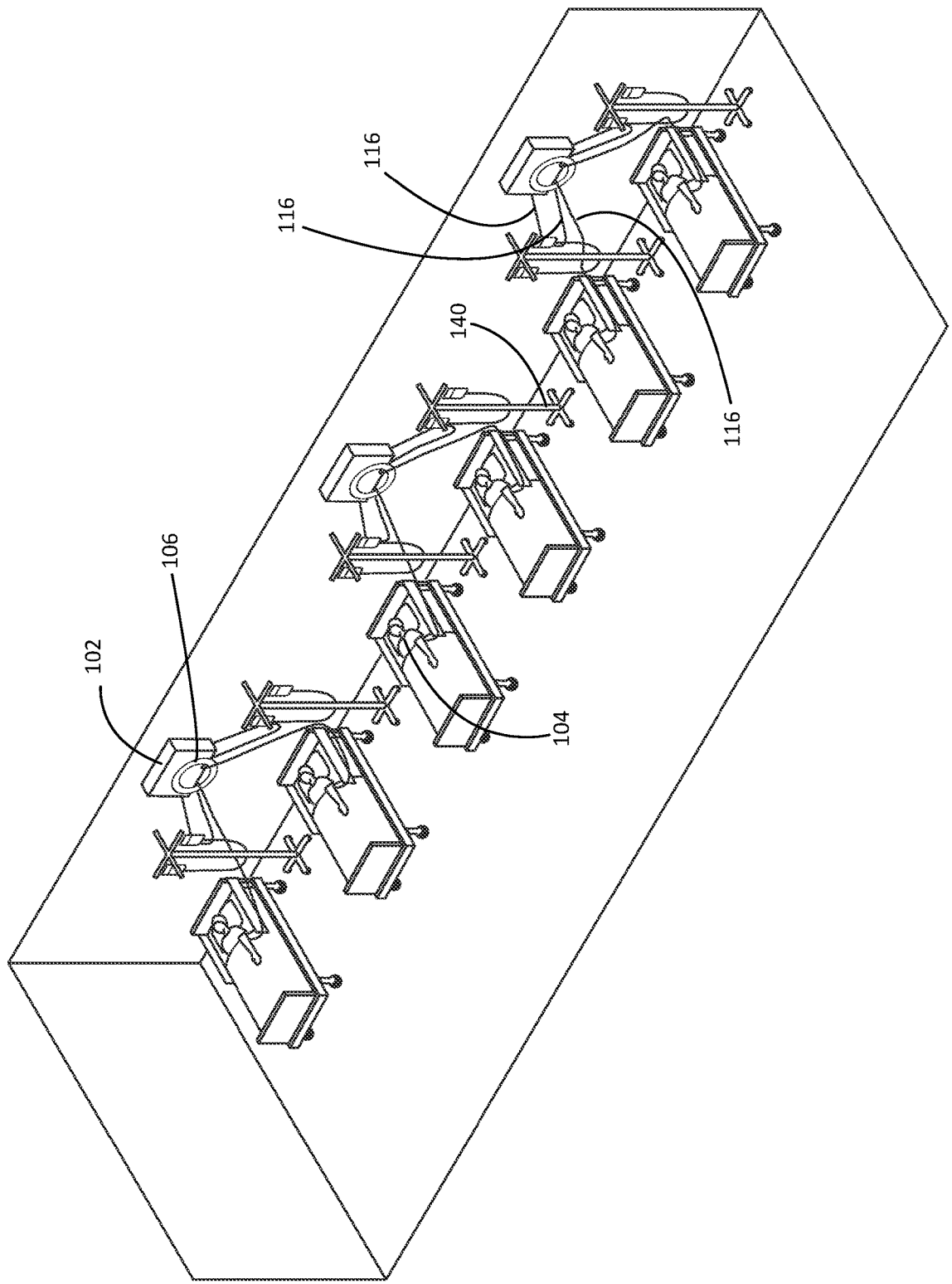
Figure 8E:
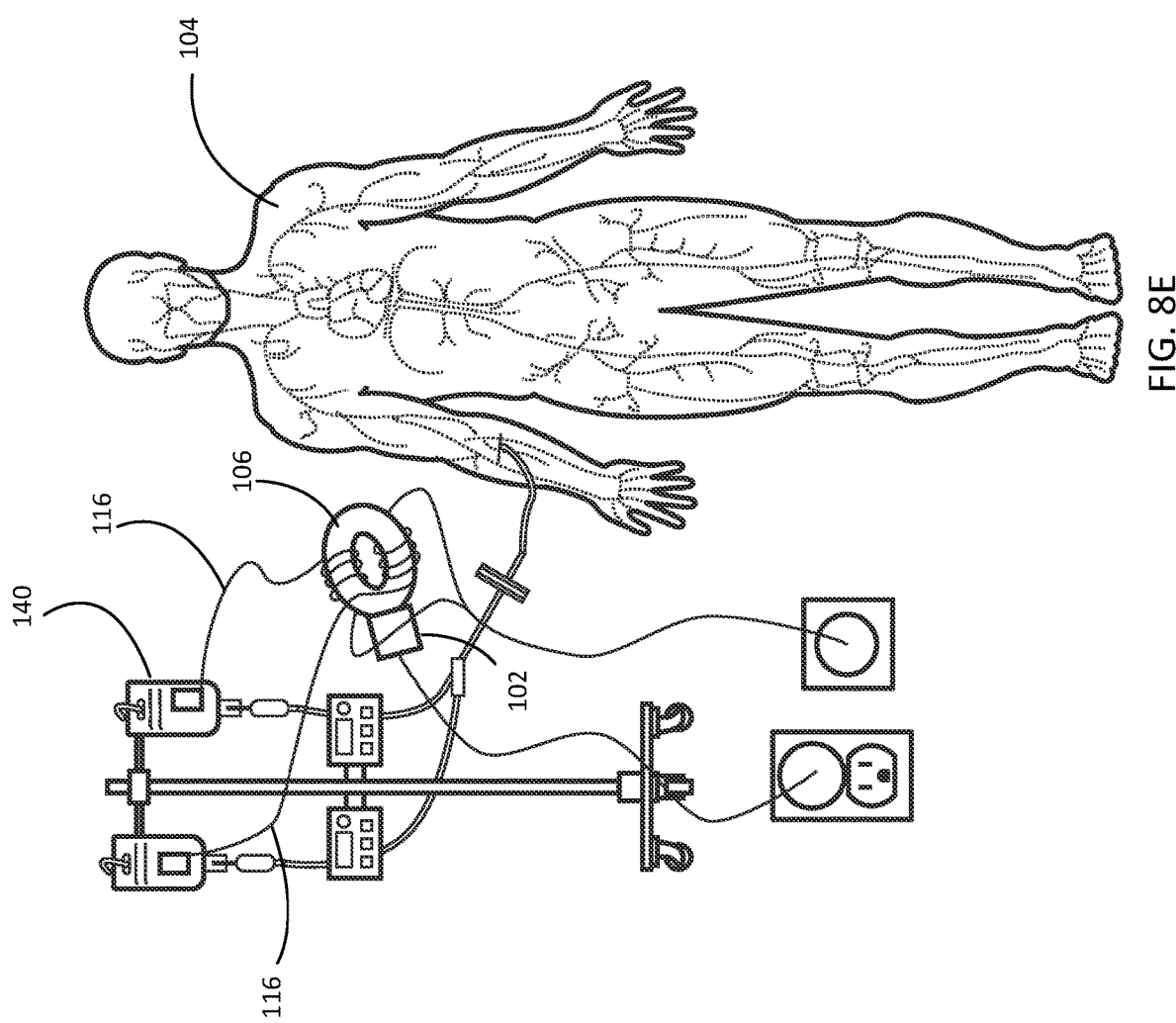

FIGS. 6A-6B illustrate embodiments with increased intensity and directionality of the electrical signal. This is accomplished by wrapping the wire 116 around the conduction ring 106 multiple times. FIGS. 7A-7B illustrate embodiments where the wire 116 wraps around the conduction ring 106 and couples with multiple users 104. FIG. 7A shows that the wire 116 may be attached directly to the users 104. Alternatively, the wire 116 may be attached to a ring 142 that passes over the head of the user 104, or may wrap around the base of the bed 144 of the user 104, as shown in FIG. 7B. FIG. 7C shows that wire 116 may be directly attached to the patients' bodies after wrapping in opposite directions around the conduction ring.

Figure 9A:
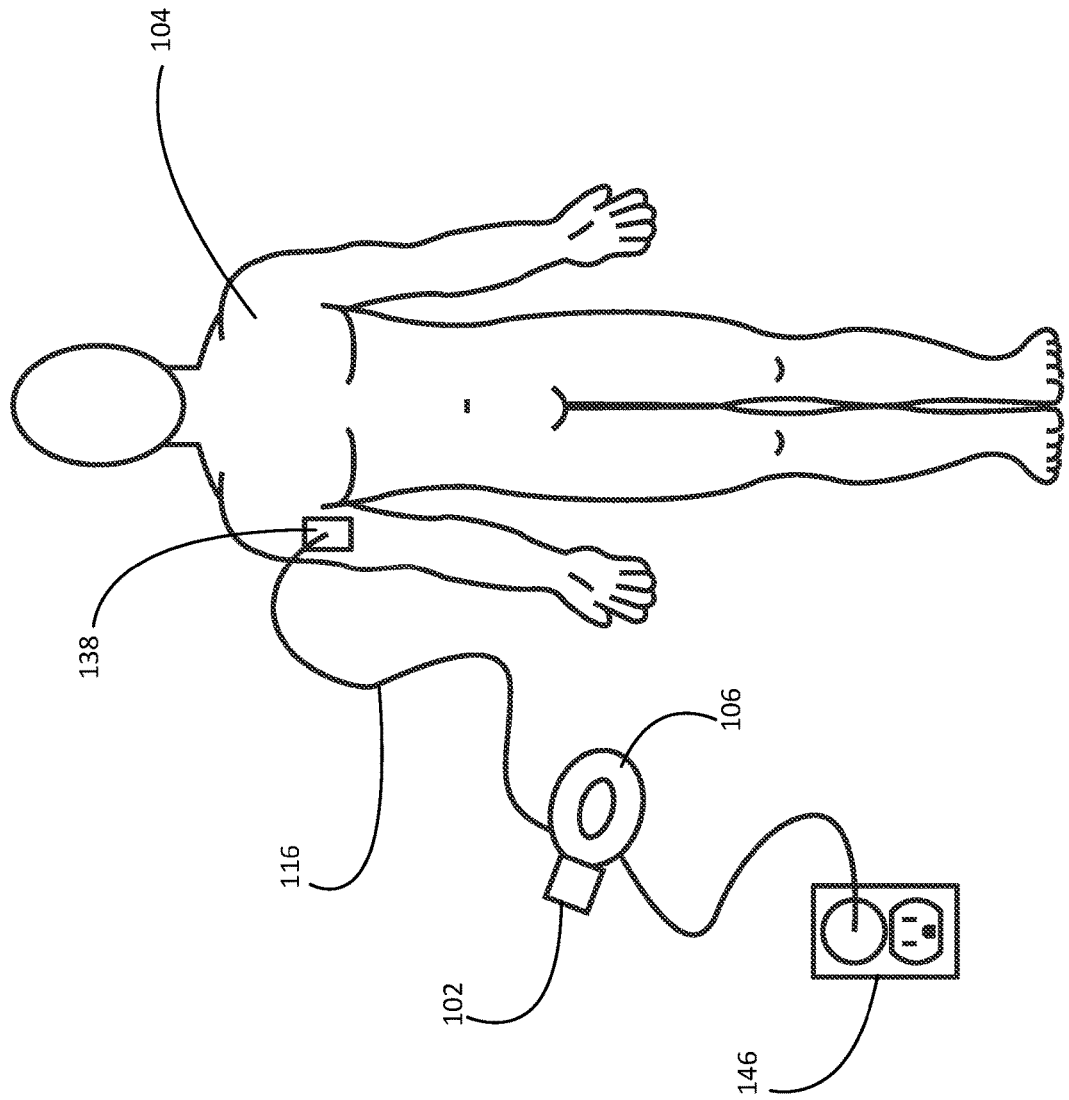
Figure 9C:
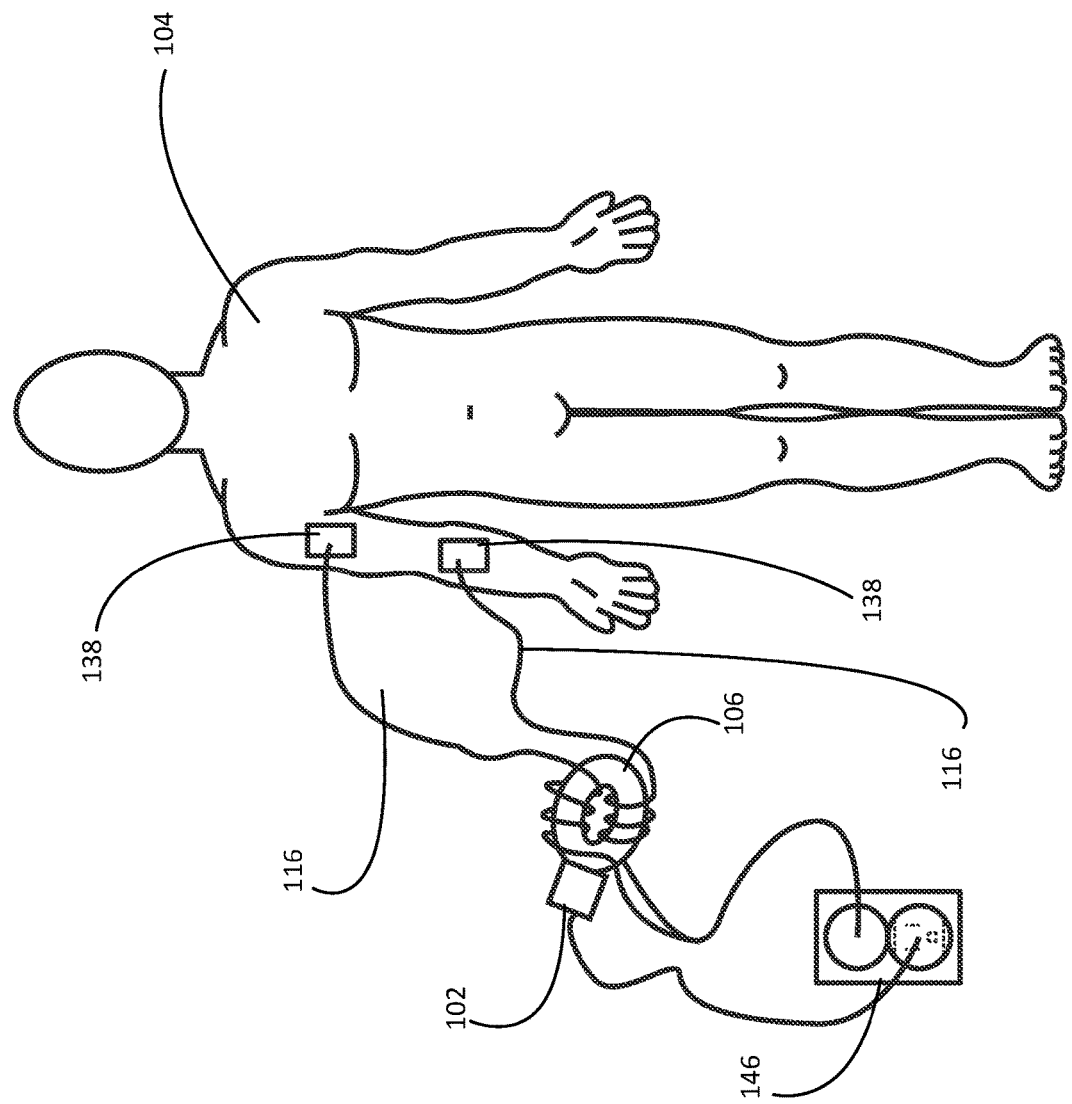

In some embodiments, the device 100 does not have a battery 114. Instead, the device 100 has an electrical plug 146 configured to plug into an electrical outlet, as shown in FIGS. 9A-9B. The device 100 thus is effectively grounded by the electrical outlet when plugged in. In such an embodiment, the conduction ring 106 may be connected to the user 104 through a wire 116, as shown in FIG. 9A. Alternatively, the conduction ring 106 may be directly worn by the user 104, as shown in FIG. 9B. FIGS. 9C and 9D depict the implementations of FIGS. 9A and 9B having a split wire wrapping in opposite directions around the conduction ring before attaching to two locations on the patient's body.

Figure 10A:
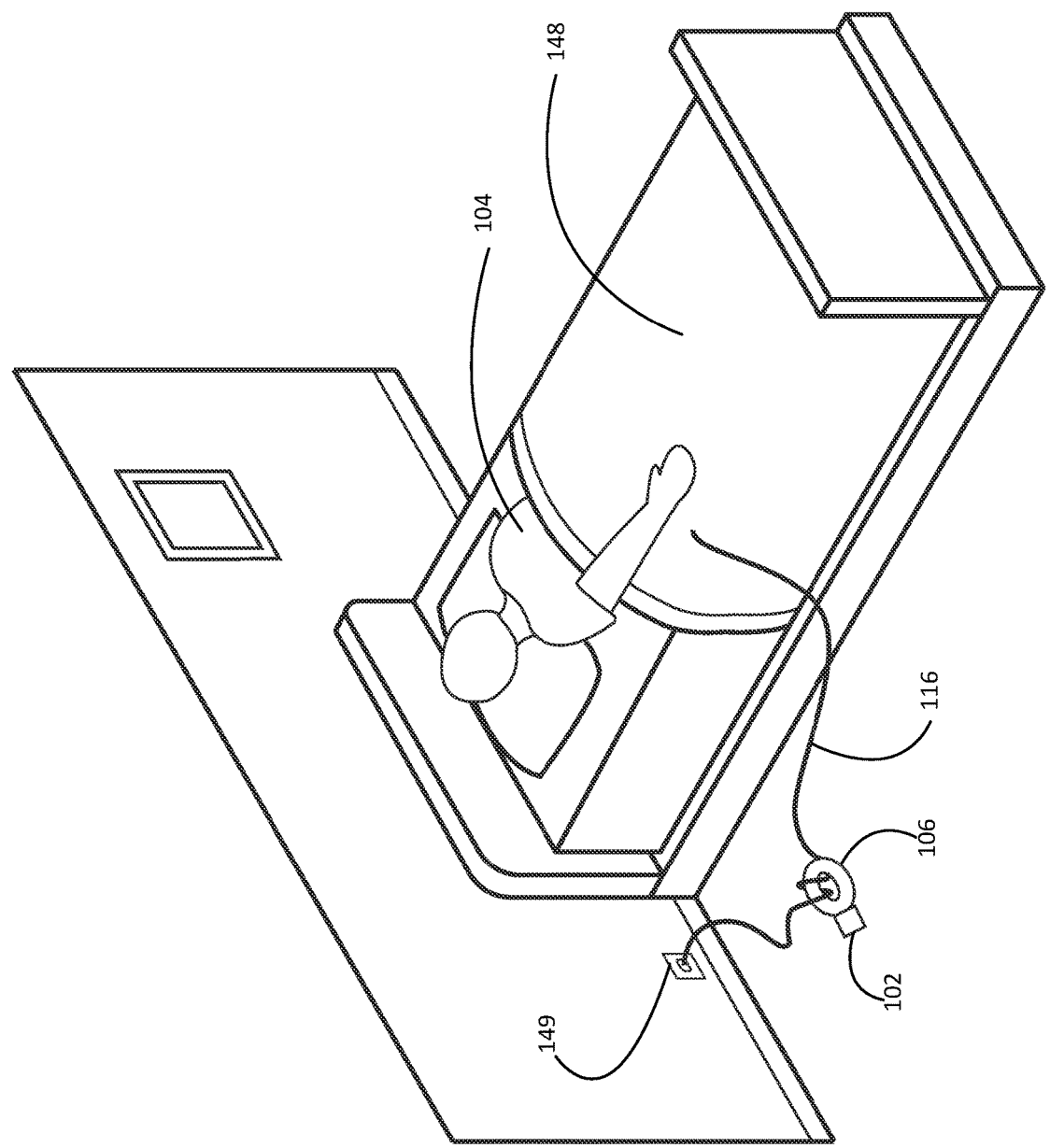
FIGS. 10A, 10B, 10C, 10D, 10E, and 10F illustrate how the device can be used with a grounding device. Preferably, the at least one wire is connected to a grounding mat or sheet and the other end of the at least one wire is grounded through a connection to a grounded outlet (FIG. 10A).
Figure 10B:
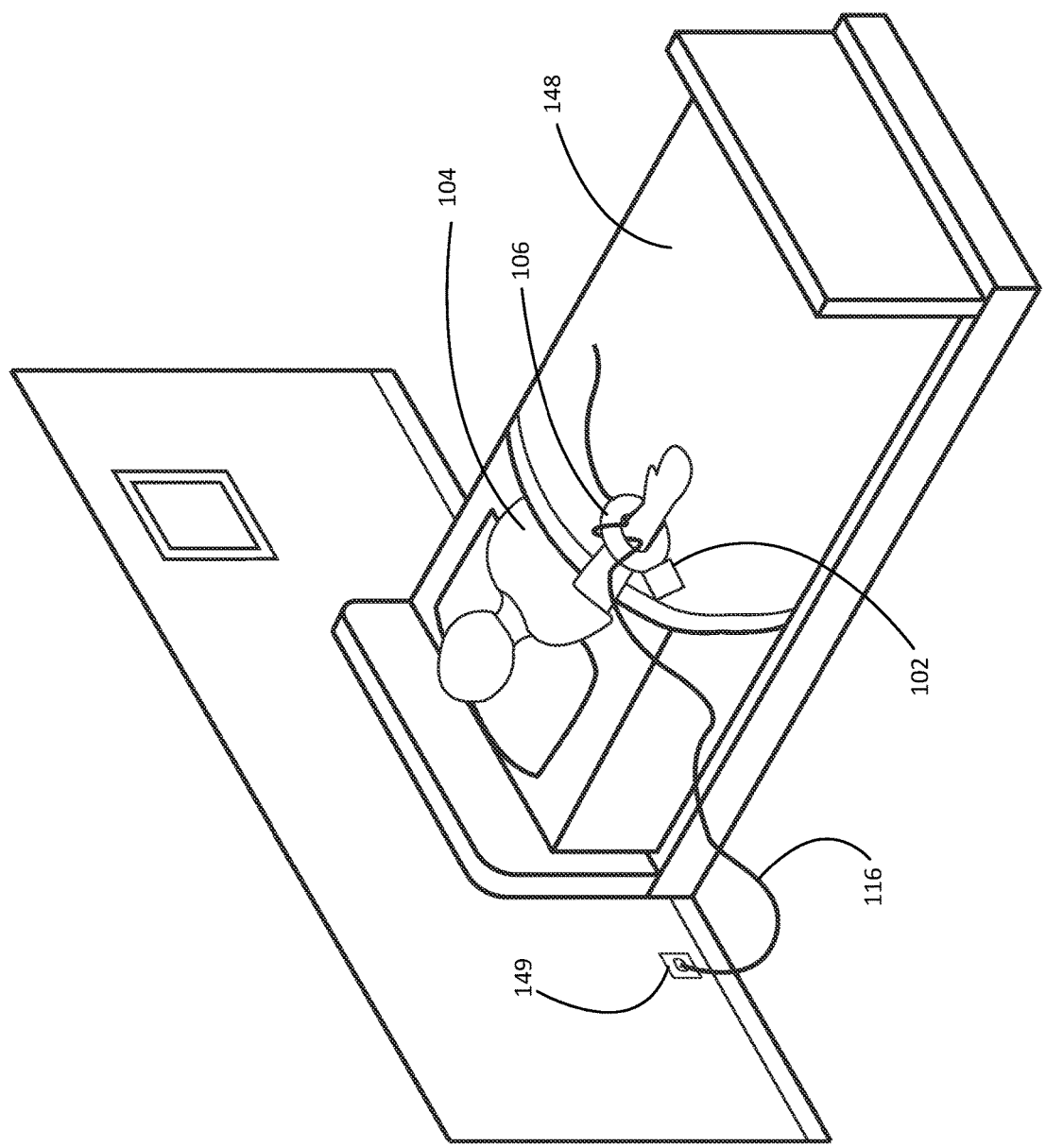
Figure 10C:
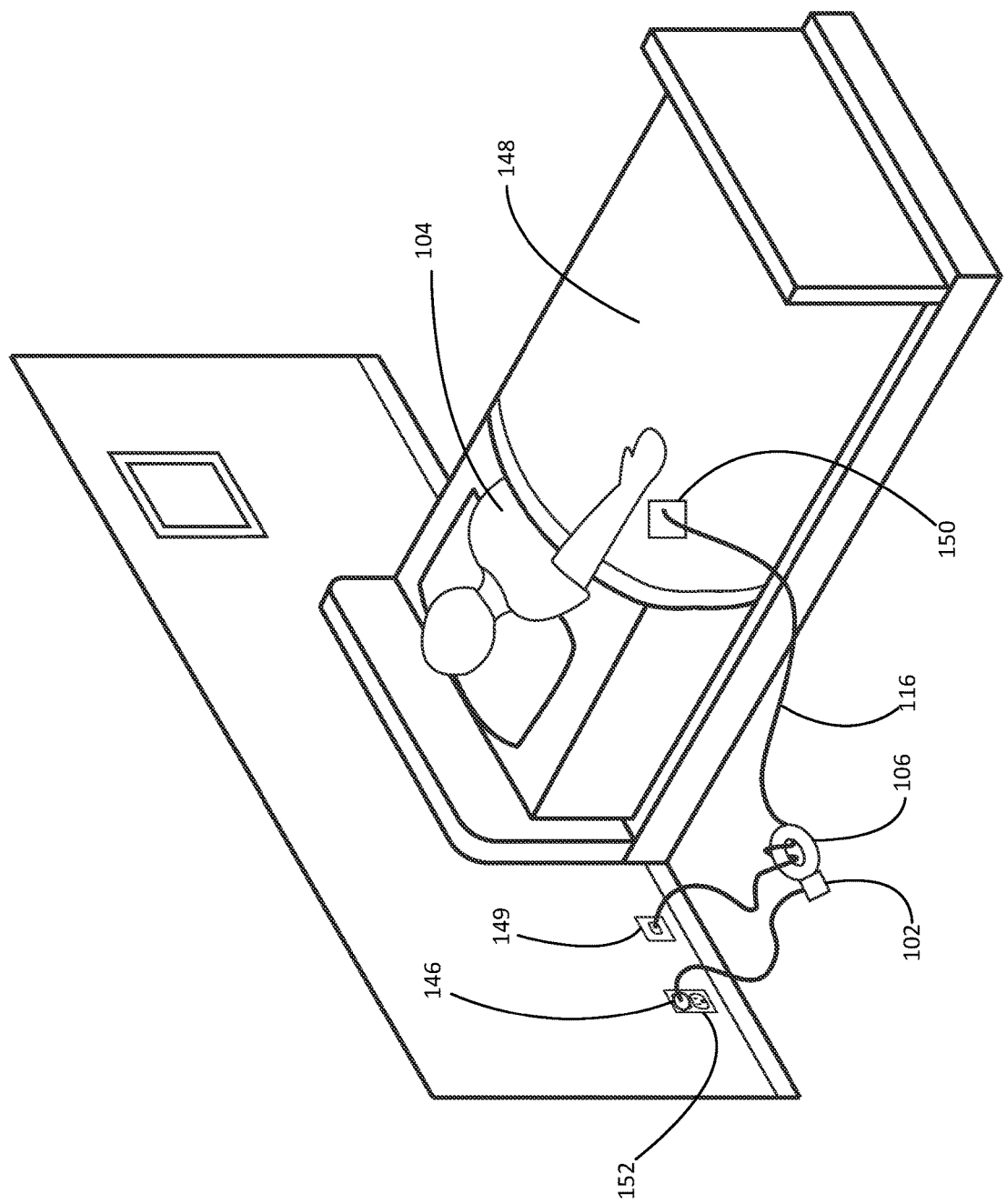

In another embodiment, the one or more wires 116 is attached to a grounded item 148, preferably a grounding sheet or mat, as illustrated in FIGS. 10A-10C. The other end of the one or more wires 116 is connected to a grounded outlet 149, preferably a grounded 110V outlet, and the ground wire is the only wire connected to the grounded outlet 149, i.e., power wires are not connected to the outlet. In one embodiment, the conductive ring 106 wraps around living tissue on the user 104 and the one or more wires 116 is connected to a grounding sheet or mat 148. FIGS. 10A-10C illustrate the grounded item 148 being used on a bed. However, the grounded item 148 could also be placed on a chair, in clothing, on a floor, in a car seat, or on some other item which the user 104 may be in contact with. As shown in FIG. 10A, the conduction ring 106 may be connected to the grounded item 148 through a wire 116. Alternatively, the user 104 may have the conduction ring 106 wrapped around a limb, with the conduction ring 106 still attached to the grounded item 148 through a wire 116, as illustrated in FIG. 10B. The device 100 may be powered by a battery 114 as disclosed above, or may be plugged into a wall outlet 152 separate from the grounded outlet 149 used to ground the grounded item 148, as shown in FIG. 10C.

Figure 10D:
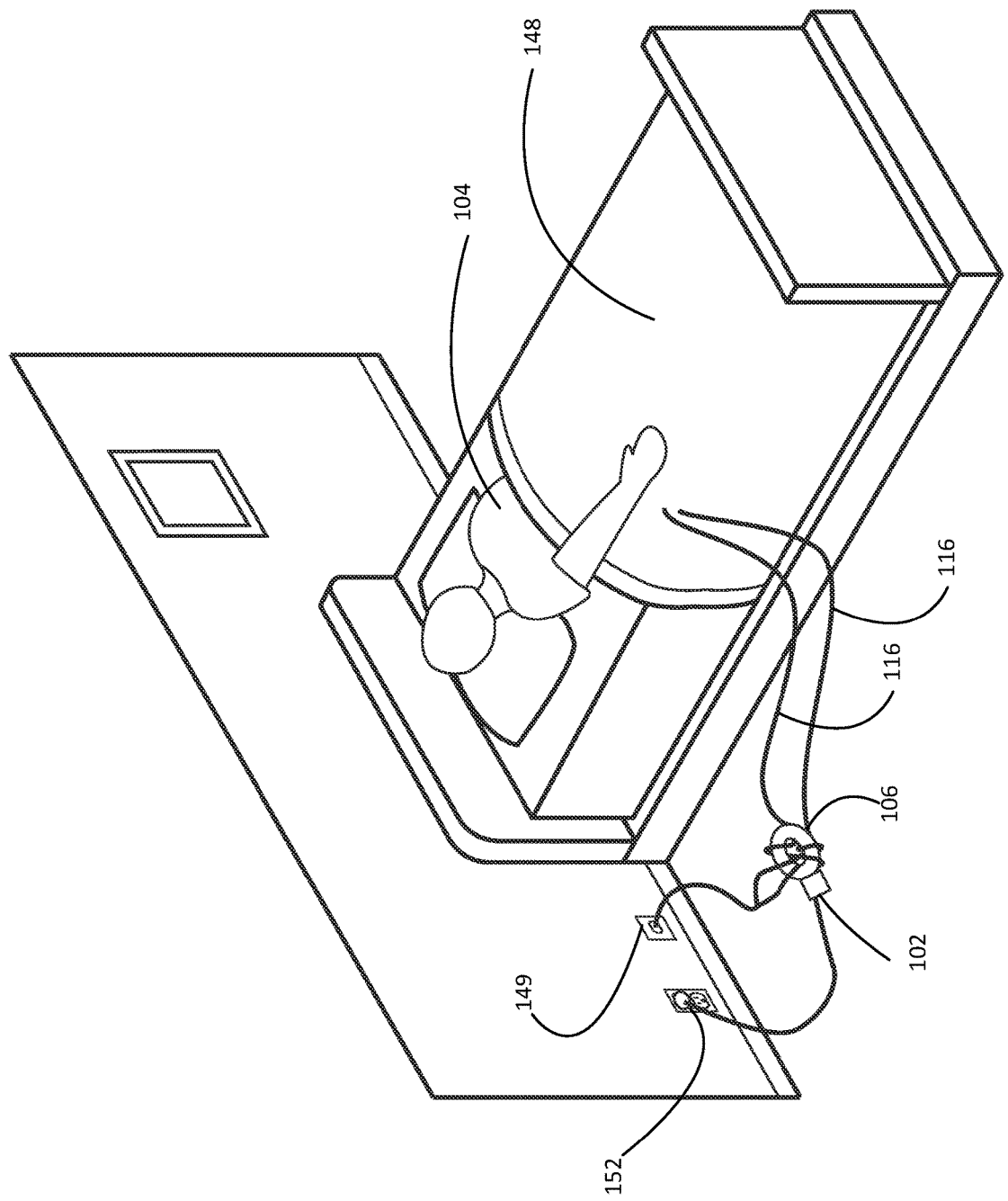
Figure 10E:
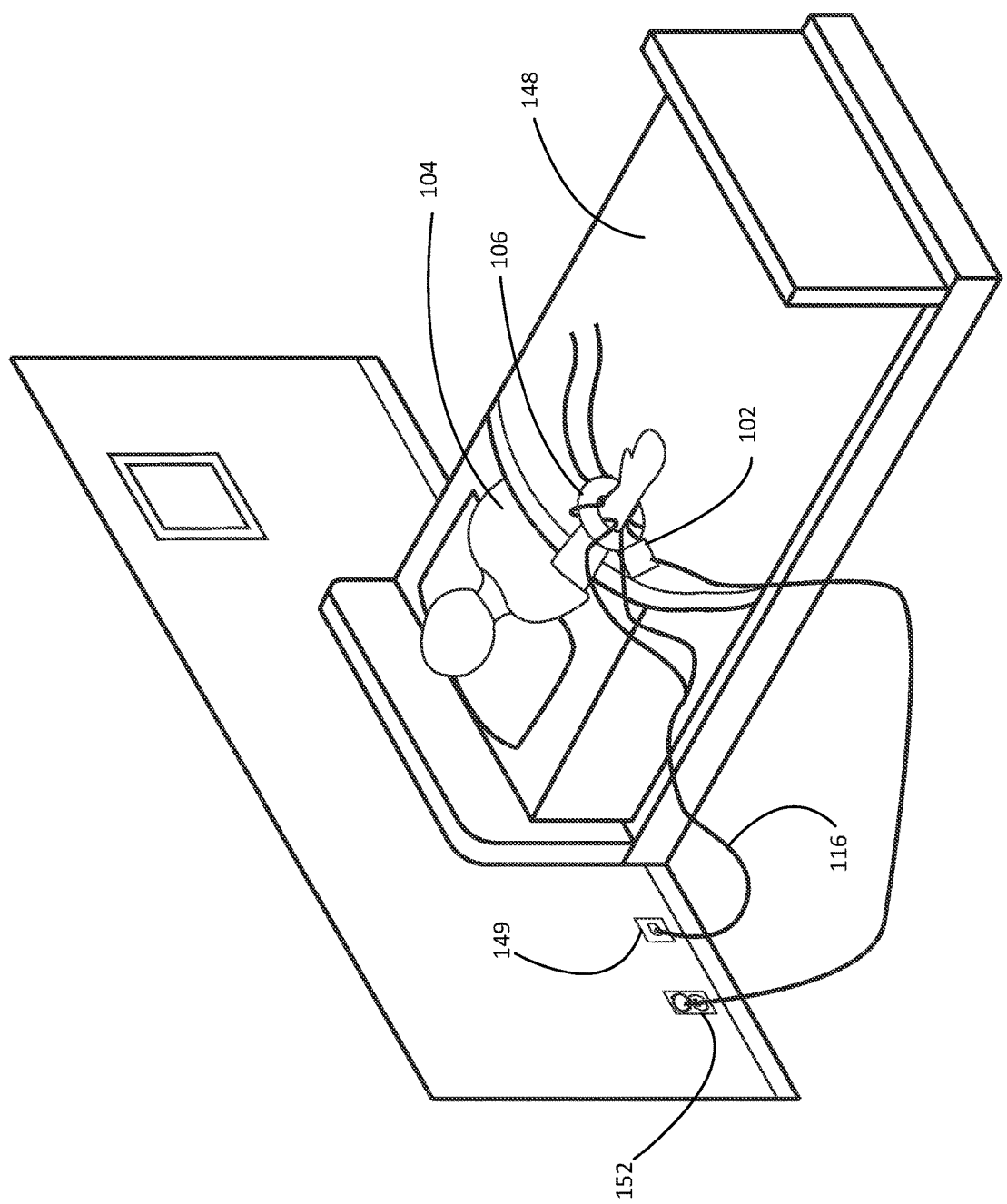
Figure 10F:
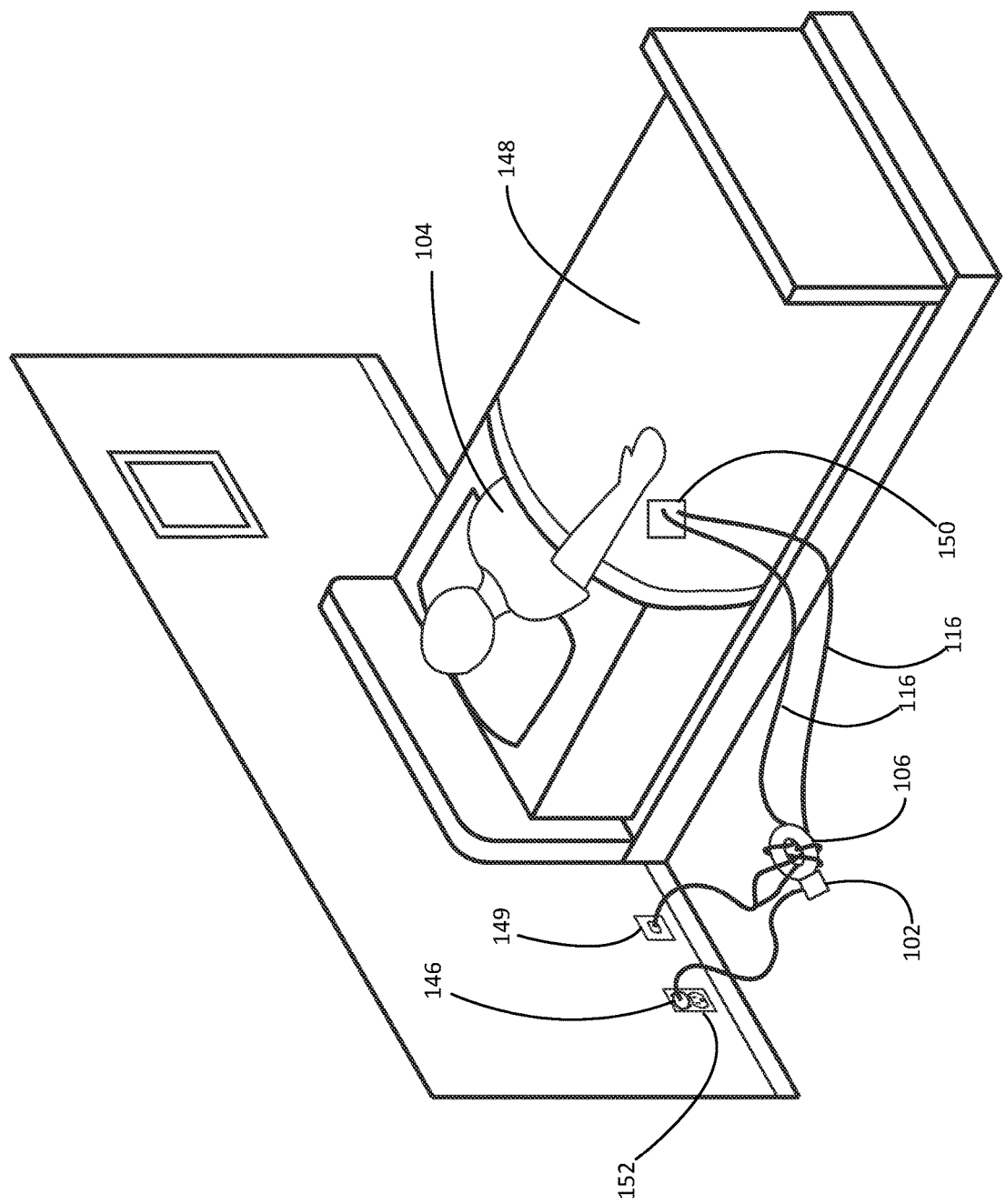

As further shown in FIG. 10C, the device 100 may comprise a volt meter 150 at the point of attachment. For example, the volt meter 150 may be at the end of the wire 116 where the wire 116 attached to the user 104. In another example, shown in FIG. 10C, the volt meter is located where the wire 116 attaches to the grounded item 148, such as the grounding mat shown. FIGS. 10D-10F depict the implementations of FIGS. 10A-10C, respectively, having a split ground wire wrapping in opposite directions around the conduction ring before connecting to the same grounding device.

A major use of the present apparatus 100 is in the treatment of tumors by selective destruction of tumor cells with substantially no effect on normal tissue cells, and thus, the exemplary apparatus is described below in the context of selective destruction of tumor cells. It should be appreciated however, that for purposes of the following description, the term "cell" may also refer to a single-celled organism (eubacteria, bacteria, yeast, protozoa), multi-celled organisms (fungi, algae, mold), and plants as parts thereof that are not normally classified as "cells". In certain implementations, the "cells" are infected by a virus and inhibition of cell growth includes prevention of further infection of cells by the virus.

The exemplary apparatus 100 enables selective destruction of cells undergoing division in a way that is more effective and more accurate (e.g., more adaptable to be aimed at specific targets) than existing methods. Further, the present apparatus 100 causes minimal damage, if any, to normal tissue and, thus, reduces or eliminates many side-effects associated with existing selective destruction methods, such as radiation therapy and chemotherapy. The selective destruction of dividing cells using the present apparatus 100 does not depend on the sensitivity of the cells to chemical agents or radiation. Instead, the selective destruction of dividing cells is based on distinguishable geometrical characteristics of cells undergoing division, in comparison to non-dividing cells, regardless of the cell geometry of the type of cells being treated.

When a cell or a group of cells are under natural conditions or environment, i.e., part of a living tissue, they are disposed surrounded by a conductive environment consisting mostly of an electrolytic inter-cellular fluid and other cells that are composed mostly of an electrolytic intra-cellular liquid. When an electric field is induced in the living tissue, by applying an electric potential across the tissue, an electric field is formed in the tissue and the specific distribution and configuration of the electric field lines defines the direction of charge displacement, or paths of electric currents in the tissue, if currents are in fact induced in the tissue. The distribution and configuration of the electric field is dependent on various parameters of the tissue, including the geometry and the electric properties of the different tissue components, and the relative conductivities, capacities and dielectric constants (that may be frequency dependent) of the tissue components.

According to one aspect of the present disclosure, the electric fields that are used are alternating fields having frequencies that are in the range from about 50 kHz to about 500 kHz, and preferably from about 80 kHz to about 300 kHz. In certain aspects, the frequencies are in the range from about 50 kHz to 500 kHz, from about 50 kHz to 450 kHz, from about 50 kHz to about 400 kHz, from about 50 kHz to about 350 kHz, from about 50 kHz to about 300 kHz, from about 50 kHz to about 250 kHz, from about 50 kHz to about 200 kHz. In other aspects, the frequencies are in the range from about 100 kHz to about 500 kHz, from about 100 kHz to about 400 kHz, from about 100 kHz to about 300 kHz, or from about 100 kHz to about 200 kHz. In yet other aspects, the frequencies are in the range from about 150 kHz to about 500 kHz, from about 150 kHz to about 400 kHz, from about 150 kHz to about 300 kHz, or from about 150 kHz to about 200 kHz.

These frequencies are sufficiently low so that the system behavior is determined by the system's Ohmic (conductive) properties but sufficiently high enough not to have any stimulation effect on excitable tissues. Such a system consists of two types of elements, namely, the intercellular or extracellular fluid, or medium and the individual cells. The intercellular fluid is mostly an electrolyte with a specific resistance of about 40-100 Ohm*cm. The cells are characterized by three elements, namely (1) a thin, highly electric resistive membrane that coats the cell; (2) internal cytoplasm that is mostly an electrolyte that contains numerous macromolecules and micro-organelles, including the nucleus; and (3) membranes, similar in their electric properties to the cell membrane, that cover the micro-organelles.

When this type of system is subjected to the present electrical fields, most of the lines of the electric field and currents tend away from the cells because of the highly resistive cell membrane and therefore the lines remain in the extracellular conductive medium. In the above recited frequency ranges, the actual fraction of electric field or currents that penetrates the cells is a strong function of the frequency.

In certain aspects, passage of the electric field through the dividing cells in late anaphase or telophase transforms the electric field into a non-homogeneous electric field that produces an increased density electric field in a region of a cleavage furrow of the dividing cells, and the electric field has amplitude and frequency characteristics such that application of the electric field prevents the cells from completing mitosis and cell division.

In certain embodiments, the disclosed method or apparatus is useful for treating neoplastic diseases. Neoplastic diseases include any malignant growth or tumor caused by abnormal or uncontrolled cell division and these diseases may spread to other parts of the body through the lymphatic system or the blood stream or nervous system. Neoplastic disease includes, without limitation, lymphoma (a neoplasm of lymph tissue that is usually malignant), carcinoma (any malignant tumor derived from epithelial tissue), leukemia (malignant neoplasm of blood-forming tissues; characterized by abnormal proliferation of leukocytes), sarcoma (a usually malignant tumor arising from connective tissue (bone or muscle etc.), and blastoma (malignancy in precursor cells). Nonlimiting examples include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

It should be appreciated that the present electronic apparatus can also be used in applications other than treatment of tumors in the living body. In fact, the selective destruction utilizing the present apparatus can be used in conjunction with any organism that proliferates by division, for example, tissue cultures, microorganisms, such as bacteria, *mycoplasma*, protozoa, fungi, algae, plant cells, etc. Nonlimiting examples of microorganisms that can be selectively destroyed using the present apparatus may be, but are not limited to, *Listeria monocytogenes, Pseudomonas* sp., *Serratia marcescens, Clostridium difficile, Staphylococcus aureus, Staphylococcus* sp., *Acinetobacter* spp., *Enterococcus* sp., *Enterobacter* sp., *Escherichia coli, Klebsiella* sp., *Streptococcus* sp., *Haemophilus influenza, Neisseria meningitides*, and *Candida* sp.

The selective destruction utilizing the present apparatus can also be used in conjunction with a virus that infects cells that undergo cellular proliferation and growth during the course of infection to enable spread and further infection of cells. Examples of viruses that may be targeted by the selective destruction of proliferating cells may be, but are not limited to, human immunodeficiency virus, cytomegalovirus, adenovirus, coronavirus, rhinovirus, rotavirus, variola virus, herpes simplex virus, hepatitis B virus, hepatitis A virus, hepatitis C virus, papillomavirus, or *influenza* virus. In one embodiment, the virus is severe acute respiratory syndrome coronavirus 2 (SARS-CoV-2) which causes coronavirus disease 2019 (COVID-19).

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1. Treatment of Bladder Cancer with ACTT Technology

A male subject was diagnosed with an aggressive type of bladder cancer. He had lost a significant amount of weight in just two months. He was initially diagnosed in 2017, and the prognosis from his doctor was poor.

A chemotherapy treatment was being utilized with limited success. The apparatus described herein was placed on the body of the subject daily to utilize the Alternating Current Tumor Treatment (ACTT) technology for treatment. The unit was placed in close proximity to the bladder to enhance the signal and to improve the effectiveness of the lines feeding the signal. The subject also slept with the unit on his body.

After several days, the subject's symptoms started to improve, and he began to regain some of the weight he had lost. His irritable bowel syndrome (IBS) symptoms greatly improved. Later, the subject went in to be evaluated for surgery. He had been on chemotherapy before. Surprisingly, when the TTF therapy was combined with the chemotherapy the tumor was not Stage 4 but a Stage 1. The subject continued the TTF with chemotherapy as the combined treatments appeared to have a synergistic effect. Several months later, he was declared cancer free, and the cancer has not returned. Even though the cancer was expected to return, to date it has not.

Example 2. Treatment of Prostate Cancer with ACTT Technology

A subject was diagnosed with inoperable prostate cancer after having previously undergone surgery to remove his prostate. The subject had received chemotherapy and was being treated with androgen deprivation therapy (ADT). The subject experienced persistent irritable bowel syndrome (IBS) including diarrhea as a side effects of these therapies.

The Prostate Specific Antigen (PSA) levels of the subject were routinely monitored. Before initiating TTF therapy with the ACTT technology, the subject's PSA levels were above normal and indicated a possible metastasis of the cancer. TTF therapy with the apparatus described herein was applied as described in Example 1. Within several days after initiation of the TTF therapy, the subject no longer experienced diarrhea or any other IBS symptoms. Not long thereafter, the subject's PSA levels dropped to normal levels. Initially the PSA levels started to drop with just one use of the TTF apparatus. Testosterone treatment was added after TTF started to have an effect. Thereafter, the PSA levels dropped to 0.01 ng/mL which is almost non-detectable. They have remained there for over a year. The patient wears the unit for 10-12 hours each day in a small backpack. If the patient removed the TTF apparatus, within 12 hours explosive diarrhea returned. Upon returning to use of the TTF apparatus, the diarrhea problem was resolved within days.

Example 3. Configurations Improving the Intensity and Directionality of the Electrical Signal It was observed that when the wire running through the conduction ring was then attached to the conduction ring itself at one end (see FIGS. 5A, 5B, 6A, and 6B), the other end of the wire exhibited an unexpectedly large voltage that when attached to the body of the patient did not drop as much as in other configurations. The voltage was at times doubled or tripled in the body with this configuration compared to configurations where the wire was not attached to the conduction ring. When one end of the wire was attached to the conduction ring itself and then passed through and/or wrapped around the conduction ring once or multiple times, greater propagation of the signal into the body resulted compared to other previously tested configurations.

Additional configurations of the device are presented in FIGS. 7 and 8. In FIG. 7A, the wire is looped through the conduction ring with the ends of the wire connected to the bodies of two different subjects. The wire is attached to the subject as described herein (e.g., with TENS or TENS-like pads). FIG. 7C is a similar configuration, with wires wrapping in opposite directions around the conduction ring before attaching to the patients' bodies. FIG. 8A portrays one possible configuration involving an IV unit feeding into the circulatory system of a subject. As the fluids in the IV unit are in direct contact with the fluids of the circulatory system, the electromagnetic signal produced by the ACTT device described herein can be propagated throughout the subject body via a connection between the device and the IV unit. FIG. 8E shows a similar configuration, with the wire splitting before wrapping around the conduction ring in opposite directions before connecting to the IV unit. In another configuration related to that shown in FIG. 8C and FIG. 8D, the conduction ring of the ACTT device encircles the tubing extending from the IV unit.

Example 4. Treatment of Viral Infection with ACTT Technology

The device described herein is worn by a patient who is suffering from a viral infection (e.g., coronavirus or *influenza* virus). The configuration of the device may be as shown in any of the Figures. Preferably, the device is worn and electromagnetic signals are applied to the infected patient for at least 10-12 hours each day.

The patient's symptoms are monitored regularly. Within a period ranging from 12 hours to a few days depending upon the severity of the infection, the symptoms from the viral infection will subside. In some cases where the viral infection causes irritation and/or inflammation of the respiratory tract, treatment with the ACTT technology will restore the respiratory tract to a healthy condition.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of inhibiting the growth of proliferating cells or viruses in living tissue of a subject, the method comprising:

applying mid-level frequency electromagnetic signals to the living tissue with a transducer comprising a magnetically conductive material passing through a conduction ring energized by an electrical signal to create the mid-level frequency electromagnetic signals within the living tissue, wherein the magnetically conductive material comprises a wire;

wherein the mid-level frequency electromagnetic signals have a mid-level frequency in a range of 50 kHz to 300 kHz;

wherein the conduction ring is energized by the transducer;

wherein circulating fluid in the living tissue provides a secondary coil for the transmission of the mid-level frequency electromagnetic signals thereby allowing for efficient transfer of energy internally within the living tissue;

wherein the inhibition of the growth of the proliferating cells or viruses is not caused by heat; and wherein the transducer further comprises at least one wire connected to a ground; and the at least one wire passes through the conduction ring and is connected to the living tissue in the subject.

2. The method of claim 1, wherein the at least one wire is connected to the conduction ring or is looped around the conduction ring at least once.

3. The method of claim 1, wherein the at least one wire is connected to the living tissue transcutaneously with Transcutaneous Electrical Nerve Stimulation (TENS) pads or TENS-like pads.

4. The method of claim 1, wherein the at least one wire is connected to an intravenous fluid therapy unit.

5. The method of claim 1, wherein the at least one wire is connected to a grounding device that is wrapped around the living tissue.

6. The method of claim 1, wherein the proliferating cells are cancer cells in a tumor and the at least one wire is connected to the living tissue at a site within 25 cm from the tumor.

7. An apparatus for inhibiting the growth of proliferating cells or viruses in living tissue of a subject, the apparatus comprising:

a transducer comprising a magnetically conductive material passing through a conduction ring energized by an electrical signal to create mid-level frequency electromagnetic signals within a living tissue, wherein the transducer is configured to generate mid-level frequency AC current electromagnetic signals in the range of 50 kHz to 300 kHz; and at least one wire forming a secondary coil connected to a ground, and passing through the conduction ring of the transducer, wherein the at least one wire is designed to be transcutaneously connected to the living tissue with Transcutaneous Electrical Nerve Stimulation (TENS) pads or TENS-like pads, and wherein the conduction ring is energized by the transducer.

8. The apparatus of claim 7, wherein the conduction ring is energized by an electromagnetic signal generated and amplified by an amplifier and transmitted wirelessly from a transmitter through an antenna, wherein the receiver is conductively coupled to the conduction ring.

9. The apparatus of claim 7, further comprising a frequency modulator that adjusts the mid-level frequency electromagnetic signals.

10. The apparatus of claim 7, wherein the conduction ring of the transducer is designed to extend around the living tissue or some portion thereof.

11. The apparatus of claim 7, wherein the magnetically conductive material is flexible.

12. The apparatus of claim 7, wherein the at least one wire is connected to the conduction ring and/or is looped around the conduction ring at least once.

* * * * *